US011351112B2

(12) United States Patent
Henry et al.

(10) Patent No.: US 11,351,112 B2
(45) Date of Patent: Jun. 7, 2022

(54) OPTIMISED SUBCUTANEOUS THERAPEUTIC AGENTS

(71) Applicant: Cantab Biopharmaceuticals Patents Limited, Valletta (MT)

(72) Inventors: William Henry, London (GB); Richard Wolf-Garraway, London (GB); John Charles Mayo, London (GB); Michael James Earl, London (GB)

(73) Assignee: Cantab Biopharmaceuticals Patents Limited, Valletta (MT)

(*) Notice: Subject to any disclaimer, the term of this patent is extended or adjusted under 35 U.S.C. 154(b) by 0 days.

(21) Appl. No.: 15/691,090

(22) Filed: Aug. 30, 2017

(65) Prior Publication Data
US 2018/0036229 A1 Feb. 8, 2018

Related U.S. Application Data

(63) Continuation of application No. 14/394,437, filed as application No. PCT/EP2013/057928 on Apr. 16, 2013, now abandoned.

(30) Foreign Application Priority Data

Apr. 16, 2012 (GB) .................................. 1206628
Aug. 1, 2012 (GB) .................................. 1213712
Aug. 22, 2012 (GB) .................................. 1214985

(51) Int. Cl.
*A61K 9/08* (2006.01)
*A61K 47/60* (2017.01)
*A61K 38/37* (2006.01)
*A61K 9/00* (2006.01)
*A61K 38/48* (2006.01)

(52) U.S. Cl.
CPC ............ *A61K 9/0019* (2013.01); *A61K 38/37* (2013.01); *A61K 38/4846* (2013.01); *A61K 47/60* (2017.08)

(58) Field of Classification Search
CPC ...... A61K 9/0019; A61K 47/60; A61K 38/37; A61K 38/4846
See application file for complete search history.

(56) References Cited

U.S. PATENT DOCUMENTS

| | | | |
|---|---|---|---|
| 4,055,635 A | 10/1977 | Green et al. | |
| 4,088,538 A | 5/1978 | Schneider | |
| 4,414,147 A | 11/1983 | Klibanov et al. | |
| 4,496,689 A | 1/1985 | Mitra | |
| 5,644,029 A | 7/1997 | Carpino | |
| 5,693,609 A | 12/1997 | Baker et al. | |
| 5,922,675 A | 7/1999 | Baker et al. | |
| 5,925,739 A | 7/1999 | Spira et al. | |
| 6,048,720 A | 4/2000 | Dalborg et al. | |
| 7,199,223 B2 * | 4/2007 | Bossard | A61K 38/37 530/383 |
| 7,612,066 B2 | 11/2009 | Suzuki et al. | |
| 7,683,158 B2 | 3/2010 | Siekmann et al. | |
| 2003/0211094 A1 | 11/2003 | Nelsestuen | |
| 2005/0113565 A1 | 5/2005 | Klausen et al. | |
| 2008/0200651 A1 | 8/2008 | Ostergaard et al. | |
| 2008/0221032 A1 | 9/2008 | Turecek et al. | |
| 2008/0255026 A1 | 10/2008 | DeFrees et al. | |
| 2009/0176967 A1 | 7/2009 | Stennicke | |
| 2009/0227504 A1 | 9/2009 | Klausen et al. | |
| 2010/0028939 A1 | 2/2010 | Behrens et al. | |
| 2010/0056428 A1 | 3/2010 | Behrens | |
| 2013/0137157 A1 | 5/2013 | DeFrees et al. | |

FOREIGN PATENT DOCUMENTS

| | | |
|---|---|---|
| CA | 2715465 A1 | 9/2009 |
| CA | 2797058 A1 | 11/2011 |
| CL | 199501746 | 9/1996 |
| CL | 2012003038 A1 | 1/2014 |
| CL | 2012003039 A1 | 1/2014 |
| EP | 0745390 A2 | 12/1996 |
| EP | 2014299 A1 | 1/2009 |
| JP | H0892294 A | 4/1996 |
| WO | WO-87/00056 A1 | 1/1987 |
| WO | WO-90/15628 A1 | 12/1990 |
| WO | WO-94/05332 A2 | 3/1994 |
| WO | WO-94/29370 A1 | 12/1994 |
| WO | WO-95/026750 A1 | 10/1995 |
| WO | WO-9832466 A1 | 7/1998 |
| WO | WO-99/43357 A1 | 9/1999 |
| WO | WO-01/58935 A2 | 8/2001 |
| WO | WO-01/082943 A2 | 11/2001 |

(Continued)

OTHER PUBLICATIONS

Coppola, A., et al. 2010 Journal of Blood Medicine 1: 183-195. (Year: 2010).*
Infusion definition by Medical dictionary: 5 pages total. (retrieved from the internet on Oct. 1, 2020). (Year: 2003).*
Aitken, "Recombinant factor VIIa," Emergency Medicine Australasia, vol. 16, pp. 446-455 (No Month Listed 2004).
Basu et al., "Structure-Function Engineering of Interferon-β1 b for Improving Stability, Solubility, Potency, Immunogenicity, and Pharmacokinetic Properties by Site-Selective Mono-PEGylation," Bioconjugate Chemistry, vol. 17, No. 3, pp. 618-630, XP008078006 (Jan. 1, 2006).
Correa, "Guidelines for the Examination of Pharmaceutical Patents: Developing a Public Health Perspective—A Working Paper," International Centre for Trade and Substainable Development; World Health Organization; United Nations Conference on Trade and Development, Jan. 2007 (64 pages).

(Continued)

*Primary Examiner* — Marsha Tsay
(74) *Attorney, Agent, or Firm* — Wilmer Cutler Pickering Hale and Dorr LLP

(57) ABSTRACT

Methods and dosage formulations are provided for subcutaneous administration in which therapeutic agents are modified to increase the hydrophilicity and molecular dimensions in relation to the native state of the therapeutic agent, in which the $C_{max}:C_{average}$ ratio is lower than the $C_{max}:C_{average}$ ratio of the agent when delivered intravenously.

5 Claims, 9 Drawing Sheets

(56) References Cited

FOREIGN PATENT DOCUMENTS

| WO | WO-2004000366 A1 | 12/2003 |
| WO | WO-2004089280 A2 | 10/2004 |
| WO | WO-2005007197 A2 | 1/2005 |
| WO | WO-2006005058 A2 | 1/2006 |
| WO | WO-2007022512 A2 | 2/2007 |
| WO | WO-2007126808 A1 | 11/2007 |
| WO | WO-2008/081024 A1 | 7/2008 |
| WO | WO-2008082669 A2 | 7/2008 |
| WO | WO-2008/127702 A2 | 10/2008 |
| WO | WO-2008119815 A1 | 10/2008 |
| WO | WO-2009/052323 A2 | 4/2009 |
| WO | WO-2009047500 A1 | 4/2009 |
| WO | WO-2009/126307 A2 | 10/2009 |
| WO | WO-2009130602 A2 | 10/2009 |
| WO | WO-2009140015 A2 | 11/2009 |
| WO | WO-2009141433 A1 | 11/2009 |
| WO | WO-2010010324 A1 | 1/2010 |
| WO | WO-2010045321 A2 | 4/2010 |
| WO | WO-2010045568 A1 | 4/2010 |
| WO | WO-2010083536 A1 | 7/2010 |
| WO | WO-2011017055 A2 | 2/2011 |
| WO | WO-2011101242 A1 | 8/2011 |
| WO | WO-2011135307 A1 | 11/2011 |
| WO | WO-2011135308 A1 | 11/2011 |
| WO | WO-2012016131 A1 | 2/2012 |
| WO | WO-2012088123 A1 | 6/2012 |

OTHER PUBLICATIONS

Di Scipio et al., "Activation of Human Factor IX (Christmas Factor)," J. Clin. Invest., vol. 61, No. 6, pp. 1528-1538 (Jun. 1978).

Du et al., "Pharmacokinetic Properties of a 40 kDa Branched Polyethylene Glycol-modified Form of Consensus Interferon-α (PEG-CIFN) in Rhesus Monkeys," Biopharmaceutics & Drug Disposition, vol. 29, pp. 481-484 (No Month Listed 2008).

Hedner et al., "Recombinant Activated Factor VII in the Treatment of Bleeding Episodes in Patients With Inherited and Acquired Bleeding Disorders," Transfusion Medicine Reviews, vol. VII, No. 2, pp. 78-83 (Apr. 1993).

International Search Report and Written Opinion issued by the European Patent Office as International Searching Authority for International Application No. PCT/EP2013/057928 dated Mar. 12, 2013 (29 pgs.).

JAPIC Clinical Trials, "International collaborative, open label, dose titration study (NN 7088-3776) to examine safety and pharmacokinetics of intravenous administration of NNC 0129-0000-1003 in hemophilia A patients", JapicCTI-No. JapicCTI-101293, Jun. 2011, Novo Nordisk Pharma Ltd., [searched on Feb. 27, 2017], 2 pages.

Jevsevar et al., "PEGylation of therapeutic proteins," Biotechnol. J., vol. 5, pp. 113-128 (No Month Listed 2010).

Jurlander et al., "Recombinant Activated Factor VII (rFVIIa): Characterization, Manufacturing, and Clinical Development," Seminars in Thrombosis and Hemostasis, vol. 27, No. 4, pp. 373-383 (No Month Listed 2001).

Karpf et al., "Pharmacokinetics and ex vivo whole blood clot formation of a new recombinant FVIII (N8) in haemophilia A dogs," Haemophilia, vol. 17, pp. e963-e968 (No Month Listed 2011).

Lacroix-Desmazes et al., "Dynamics of factor VIII interactions determine its immunologic fate in hemophilia A," Blood, vol. 112, No. 2, pp. 240-249 (Jul. 15, 2008).

Mcmullen et al., "Locations of disulfide bonds and free cysteines in the heavy and light chains of recombinant human factor VIII (antihemophilic factor A)," Protein Science, vol. 4, pp. 740-746 (No Month Listed 1995).

O'Hara et al., "Nucleotide sequence of the gene coding for human factor VII, a vitamin K-dependent protein participating in blood coagulation," Proc. Natl. Acad. Sci. USA, vol. 84, pp. 5158-5162 (Aug. 1987).

Peng et al., (2012), The AAPS Journal 14(1): 35-42.

Rivkin, "Certolizumab Pegol for the Management of Crohn's Disease in Adults," Clinical Therapeutics, vol. 31, No. 6, pp. 1158-1176 (No Month Listed 2009).

Roberts et al., "The use of recombinant factor VIIa in the treatment of bleeding disorders," Blood, vol. 104, No. 13, pp. 3858-3864 (Dec. 15, 2004).

Shaunak et al., "Site-specific PEGylation of native disulfide bonds in therapeutic proteins," Nature Chemical Biology, vol. 2, No. 6, pp. 312-313 (Jun. 2006).

Shen et al., "The tertiary structure and domain organization of coagulation factor VIII," Blood, vol. 111, No. 3, pp. 1240-1247 (Feb. 1, 2008).

Stennicke et al., "Generation and biochemical characterization of glycoPEGylated factor VIIa derivatives," Thromb. Haemost., vol. 100, pp. 920-928 (No Month Listed 2008).

Wang et al., "Coagulation factor VIII: structure and stability," International Journal of Pharmaceutics, vol. 259, pp. 1-15 (No Month Listed 2003).

Shi et al., "Intravascular recovery of VWF and FVIII following intraperitoneal injection and differences from intravenous and subcutaneous injection in mice," Haemophilia, Jul. 2012, vol. 18(4): 639-646. Author manuscript, 16 pages.

* cited by examiner

OPTIMISED SUBCUTANEOUS THERAPEUTIC AGENTS

RELATED APPLICATION

This is a continuation application which claims the benefit of and priority to U.S. application Ser. No. 14/394,437, filed Oct. 14, 2014, which is a 371 U.S. National Stage Application of International Patent Application No.: PCT/EP2013/057928, filed on Apr. 16, 2013, which claims priority to GB1214985.2 filed Aug. 22, 2012, GB1213712.1, filed Aug. 1, 2012, and GB1206628.8 filed Apr. 16, 2012, the contents of which are hereby incorporated by reference in their entirety.

INCORPORATION BY REFERENCE

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

TECHNICAL FIELD

The present invention relates to the subcutaneous delivery of therapeutic agents, as well as the modifications of such agents to render them suitable for subcutaneous delivery.

BACKGROUND

Many hydrophobic (lipophilic) molecules are used in the treatment of infection, disease and disorders. Lipophilic molecules are generally administered directly into the bloodstream of a patient, in order to ensure rapid delivery to the site of the infection, disease etc. However, the half life and/or bioavailability of such molecules may be sub-optimised. Disadvantages of intravenous administration include local and general reactions to the delivery of relatively large amounts of agent into a patient and the inconvenience of intravenous administration.

SUMMARY

The present inventors have surprisingly found that modifying a therapeutic agent, and thereby increasing the hydrophilicity and the molecular dimensions of the agent, results in the inability of such an agent to directly enter the vascular system. However, the modified agent still becomes bioavailable due to its ability to enter the circulatory system of a patient via the aqueous lymphatic system. The modification is chosen in order to reduce surface adherence of the therapeutic agent to the connective tissues and to increase its solubility in tissue fluid. The modified therapeutic agents of the present invention are particularly useful when they are delivered to the subcutaneous space, since they are too large to enter the vascular system directly from the subcutaneous space and therefore are transported around the body by the lymphatic system, entering the circulatory system via the thoracic duct (right lymphatic duct and subclavian veins). This surprisingly results in a predictable, steady infusion of the agent into the circulatory system of the patient. Accordingly, the present invention is concerned with the subcutaneous delivery of a modified agent, in order to render the effect of the modified agent more predictable in its longevity, infusion rate and elimination rate and thus duration of effect. This is achieved by causing the agent to be more hydrophilic and modifying its molecular dimensions such that upon subcutaneous delivery to the patient, the modified agent is unable to pass through the blood vessel walls to enter the blood stream but is transported by interstitial fluid such that it enters the lymphatic system. This results in a controlled, predictable release into the vascular system, from the lymphatic system. It removes the need to consider the level of vascularisation around a site of delivery as discussed below.

The invention can be applied to peptides, biomolecules, including all blood factors, hormones, antibiotics, monoclonal antibodies and some small molecules. Any suitable modification can be used that does not interfere with the therapeutic effect of the molecule, and that increases the hydrophilicity and, modifies its molecular dimensions (which may include molecular weight, or the physical size of the modified agent) to ensure that it cannot directly enter the vasculature without first passing into the subclavian vein via the lymphatic system at the thoracic duct. The chosen modification may have the concomitant effect of regulating the elimination of the agent from the body (by excretion, digestion, immunologic attack or other means) such that the rate of infusion and rate of elimination of the agent are "balanced" for an optimal therapeutic effect.

Examples of suitable modifications include the conjugation of the agent with a polymer, suitably a biocompatible polymer, such as polyethylene glycol (PEG), poly-phosphatidyl choline (PC), polypropylene glycol (PPG), copolymers of ethylene glycol and propylene glycol, polyethylene oxide (PEO), polyoxyethylated polyol, polyolefinic alcohol, polyhydroxyalkylmethacrylate, polysaccharides, poly α-hydroxy acid, polyvinyl alcohol, polyphosphosphasphazene, poly N-acryloylmorpholine, polyalkyene oxide polymers, polymaleic acid, poly DL-alanine, carboxymethylcellulose, dextran, starch or starch derivatives, hyaluronic acid, chitin, polymethacrylates, polysialic acid (PSA), polyhydroxy alkanoates, poly amino acids and combinations thereof. The biocompatible polymer may have a linear or branched structure.

Other examples of biocompatible polymers are a protein selected from, but not limited to, the group consisting of albumin, transferrin, immunoglobulins including monoclonal antibodies, antibody fragments for example; single-domain antibodies, $V_L$, $V_H$, Fab, F(ab')$_2$, Fab', Fab3, scFv, di-scFv, sdAb, Fc and combinations thereof.

Other methods of modifying the therapeutic agent might be through the use of fusion proteins; incorporation into vesicular delivery vehicles such as liposomes, transfersomes or micelles; incorporation into/attachment to dendrimers; formation of oligomer complexes of the agent. The chosen modification may have the concomitant effect of regulating the elimination of the agent from the body (by excretion, digestion, immunologic attack or other means) such that the rate of infusion and rate of elimination of the agent are "balanced" for an optimal therapeutic effect.

Once delivered to the subcutaneous space the modified agent thus located is able to be transported via the lymphatic system to infuse into the vascular system via the subclavian veins, after which such modifications also control the elimination of the agent from the body in such a way that the ratio of infusion rate from the subcutaneous space into the circulation to elimination rate of the drug product from the body may be balanced and controlled in a manner to optimise the therapeutic efficiency and effectiveness of the modified agent.

An example of therapeutic agents that may be modified for subcutaneous delivery in this way include blood coagulation factors. The blood coagulation cascade involves a number of different proteins which variously serve to activate each other and promote the formation of a blood clot and maintain healthy haemostasis. In some embodiments, the blood coagulation factor to be modified in accordance with the invention is selected from the group consisting of Factor VII, Factor VIIa, Factor VIII, Factor IX, Factor X, Factor Xa, Factor XI, Factor VIIa, Factor V, Factor XIII, von Willebrand's Factor and Protein C. In some embodiments the blood coagulation factor is suitably Factor VII, Factor VIII or Factor IX.

An example of therapeutic agents to which the invention relates includes, blood coagulation Factor VII (herein referred to as FVII), which is a 53,000 Dalton (Da), glycosylated, Vitamin K dependent, single-chain zymogen, containing 12 native disulphide bonds (O'Hara et al., *Proc. Nat'l Acad. Sci. USA,* 84: 5158-5162 (1987)). The protein is predominantly produced in the liver. FVII is involved in the extrinsic blood clotting cascade (FIG. 1). The protein is organised into four discrete domains: an N-terminal γ-carboxyglutamate (Gla) domain, two epidermal growth factor-like (EGF) domains and a C-terminal serine protease domain. The circulating zymogen shows very little protease activity in the absence of its cofactor tissue factor (TF) which is found in the vascular subendothelium. Following vascular damage, FVII binds to TF with high affinity and is converted to the active, two-chain enzyme FVIIa by specific cleavage of the peptide bond between arginine 152 and isoleucine 153. The FVIIa light-chain is composed of the N-terminal Gla and EGF-like domains and the heavy-chain is composed of the serine protease domain. The heavy and light chains are held together by a single disulphide bond between cysteine 135 and cysteine 262. Once activated, FVIIa rapidly catalyses the conversion of FX to FXa and FIX to FIXa. FXa then forms a complex with FVa to cleave prothrombin, resulting in the generation of small amounts of thrombin (Aitken, M. G. *EMA,* 16: 446-455 (2004)). This thrombin generation activates platelets and cofactors V, VIII and XI on the platelet surface. The activation leads to the formation of a thrombin burst which causes fibrin polymerisation and the formation of a haemostatic plug.

Human recombinant FVIIa has been developed and commercialised by Novo Nordisk as NovoSeven® (eptacog alfa [activated], ATC code B02BD08). NovoSeven® is licensed for the treatment of bleeding episodes in haemophilia A or B patients who have developed inhibitory antibodies against FVIII or IX, respectively (Jurlander et al., *Seminars in Thrombosis and Hemostasis,* 27: 373-383 (2001); Roberts et al., *Blood,* 15: 3858-3864 (2004)). The treatment has proved to be safe and effective since its launch in 1996. However, due to the proteins relatively short in vivo half-life (2.3 hours; Summary Basis for Approval NovoSeven®, FDA reference number 96-0597) multiple infusions of high doses of the product (90 μg kg$^{-1}$) may be required over time during a single bleeding episode in order to attain haemostasis. The short half-life of the product and the high dose required to render the desired therapeutic effect preclude the common use of NovoSeven® for prophylactic treatment of haemophiliacs with inhibitors. Clearly, therefore, there is a need for the development of FVIIa molecules which have an increased half-life, producing improvements in pharmacokinetics (PK) and pharmacodynamics (PD).

Factor VIII (FVIII) is an essential blood clotting factor also known as anti-haemophilic factor (AHF). In humans, Factor VIII is encoded by the F8 gene. Defects in this gene results in haemophilia A, a well-known recessive X-linked coagulation disorder effecting approximately 1 in 5,000 males.

The X-linked F8 gene encodes a polypeptide of 2351 amino acids from 26 exons which after signal peptide cleavage renders a mature FVIII molecule of 2332 amino acids (Wang et al. *Int. J. Pharmaceutics,* 259: 1-15 (2003)). FVIII has been found to be synthesized and released into the bloodstream by the vascular, glomerular, and tubular endothelium, and the sinusoidal cells of the liver though there is still considerable ambiguity as to what the primary site of release in humans is. The FVIII molecule is organised into six protein domains; NH2-A1-A2-B-A3-C1-C2-COOH. The mature molecule contains a number of post-translational modifications including N-linked and O-linked glycosylation, sulphonation and disulphide bond formation. FVIII contains a total of 23 cysteine residues, 16 of these form 8 disulphide bonds in the A and C domains of the protein (McMullen et al. *Protein Science,* 4: 740-746 (1995)). Due to the post-translational modification of the protein, its circulation molecular weight can be up to 330 kDa depending on the level and type of glycosylation. FVIII is also proteolytically processed so that the circulating species is a heterodimer composed of a heavy chain (A1-A2-B) and light chain (A3-C1-C2). When FVIII is secreted into the circulation it binds to von Willebrand Factor (vWF) in a non-covalent manner. The binding of the two molecules involves the A3 and C2 domains of the light chain of FVIII (Lacroix-Desmazes et al. *Blood,* 112: 240-249 (2008)). Binding to vWF increases the stability and circulating half-life of FVIII. Although binding to vWF increases the circulating half-life of FVIII, its native half-life is 15-19 hours.

Factor VIII is an essential cofactor participating in the intrinsic blood coagulation pathway. Its role in the coagulation cascade is to act as a "nucleation template" to organise the components of the FXase complex in the correct spatial orientation on the surface of activated platelets (Shen et al. *Blood,* 111: 1240-1247 (2008)). FVIII is initially activated by thrombin (Factor IIa) or FXa and it then dissociates from vWF in the form of FVIIIa. FVIIIa then binds to activated platelets at the site of vascular injury and binds FIXa through an A2 and A3 mediated interaction. The binding of FIXa to FVIII in the presence of Ca$^{2+}$ on the platelet surface increases the proteolytic activity of FIXa by approximately 200,000-fold. This complex then activates FX to FXa. Factor Xa, with its cofactor Factor Va, then activates more thrombin. Thrombin in turn cleaves fibrinogen into fibrin which then polymerizes and crosslinks (using Factor XIII) into a fibrin blood clot.

No longer protected by vWF, activated FVIII is proteolytically inactivated in the process (most prominently by activated Protein C and Factor IXa) and quickly clears from the blood stream.

Factor IX (also known as Christmas factor) is a serine protease of the coagulation system and deficiency of this protein causes hemophilia B. Factor IX is produced as an inactive zymogen precursor which is subsequently processed to remove the signal peptide, followed by further glycosylation and subsequent cleavage by Factor XIa or Factor VIIa to produce a two-chain form linked by a disulfide bridge (Scipio et al *J Clin Invest.* 1978; 61(6): 1528-1538). Once activated as Factor IXa and in the presence of Ca$^{2+}$, membrane phospholipids, and a Factor VIII cofactor, it hydrolyses an arginine-isoleucine bond in Factor X to form Factor Xa. Factor IX is inhibited by antithrombin.

Haemophilia B is an X-linked bleeding disorder caused by a plethora of mutations in the factor IX gene, resulting in a deficiency of effective procoagulant protein. Haemophilia B which is also known as Christmas disease, is the consequence of non-functional or deficient FIX which prevents normal initiation of the intrinsic cascade. Serious and potentially life threatening bleeding events can develop with this condition which can be corrected by timely administration of an adequate amount of FIX. Haemostasis can be maintained for as long as the circulating zymogen is in the therapeutic range.

Historically, Haemophilia B has been treated by intravenous delivery of plasma FIX or prothrombin complex concentrates and more recently by highly purified plasma derived and recombinant FIX. The advent of recombinant human FIX from Chinese hamster ovary cells (CHO cells) has transformed the treatment of Christmas disease to the point where prophylactic therapy is now possible particularly in small children. The limiting factor in this regard however is the short half-life and potential "super potency" of which has constrained prophylactic therapy to approximately 3 day intervals.

One of the problems faced by physicians seeking to treat patients with blood clotting and other disorders is how to achieve a long-lasting therapeutic dosage of a therapeutic agent, such as a blood clotting factor composition administered to such patients. Another problem, particularly around the prophylactic use of such agents is maintaining a predictable, steady state level of infusion, distribution and elimination of therapeutic agents in the body, thus avoiding the sawtooth "bursts" or "peaks" of levels of both the agent and its effects.

For example, the regulation of blood coagulation is a process that presents a number of leading health problems, including both the failure to form blood clots as well as thrombosis, the formation of unwanted blood clots. Agents that prevent unwanted clots are used in many situations and a variety of agents are available. Unfortunately, most current therapies have undesirable side effects. Orally administered anticoagulants such as Warfarin act by inhibiting the action of vitamin K in the liver, thereby preventing complete carboxylation of glutamic acid residues in the vitamin K-dependent proteins, resulting in a lowered concentration of active proteins in the circulatory system and reduced ability to form clots. Warfarin therapy is complicated by the competitive nature of the drug with its target. Fluctuations of dietary vitamin K can result in an over-dose or under-dose of Warfarin. Fluctuations in coagulation activity are an undesirable outcome of this therapy.

Injected substances such as heparin, including low molecular weight heparin, also are commonly used anticoagulants. Again, these compounds are subject to overdose and must be carefully monitored.

Another phenomenon that limits the usefulness of therapeutic peptides is the relatively short in vivo half-life exhibited by some of these peptides. Overall, the problem of short in vivo half-life means that therapeutic glycopeptides must be administered frequently and in high dosages, which ultimately translate to higher risk of local adverse reactions and higher health care costs than might be necessary if a more efficient method for maintaining therapeutically effective levels of glycoprotein therapeutics for longer was available.

The ability to ensure the delivery of therapeutic agents via the lymphatic system provides controlled infusion of the agent. The increased hydrophilicity also assists in concealing the molecule from damage by degrading enzymes, the immune system etc. Furthermore, the increased mobility in water renders the therapeutic agents more bioavailable, leading to lower dosage requirements. This in turn may result in fewer side effects, more efficient treatment and less time spent in a physician's care.

The inventors have surprisingly shown that a more consistent 'steady state' level of therapeutic agent can be achieved systemically when modified in accordance with the invention and delivered to the subcutaneous space. This increased consistency in 'steady state' can be attributed to a combination of rate of introduction into the vascular system via the lymphatic system (i.e. infusion), balanced against the rates of metabolism and/or immune system degradation, and rate of elimination via the kidneys or GI tract.

The subcutaneous delivery of a modified agent in accordance with the present invention may, therefore, allow the 'sawtooth' peaks and troughs commonly seen with repeated bolus injection delivery to be mitigated. However a larger dose can be administered by subcutaneous delivery such that $C_{max}$ is the same as achieved by intravenous injection, in which case a longer duration of the therapeutic effect of the modified agent will be achieved due to the slower rate of infusion via the lymphatic system into the vascular system. Thus, the present invention may result in less frequent administration. Alternatively, the same administration frequency could be envisaged with a lower dose when subcutaneous delivery is employed in accordance with the invention, instead of intravenous delivery.

In other words, over a given duration (such as 4 days) the ratio of $C_{max}:C_{average}$ of a subcutaneously administered dose of a modified agent is lower than when the same dose is administered intravenously. This is clearly an advantage since the levels of the modified agent in the bloodstream are more consistent.

As one of skill in the art will appreciate, a lower $C_{max}$ may be of benefit to the patient, as is a lower ratio of $C_{max}:C_{average}$ or $C_{max}:C_{min}$ (i.e. a flattened graph of peaks and troughs when compared to the typical "sawtooth" profile of an intravenously administered drug).

Factor VIIa, for example, illustrates this problem and the modification shows the inventive solution thereto. Factor VII and VIIa have circulation half-times of about 2-4 hours in the human. That is, within 2-4 hours, the concentration of the peptide in the serum is reduced by half. When Factor VIIa is used as a procoagulant to treat certain forms of haemophilia, the standard protocol is to inject VIIa every two hours and at high dosages (45 to 90 µg/kg body weight). See, Hedner et al., Transfus. Med. Rev. 7: 78-83 (1993)). Thus, use of these proteins as procoagulants or anticoagulants (in the case of factor VII) requires that the proteins be administered at frequent intervals and at high dosages.

The conjugation of biopharmaceuticals to biocompatible polymers has previously been used successfully to improve the physicochemical characteristics of such therapeutic products. Characteristics of proteins which have been improved through conjugation include PK, PD and immunogenicity. The attachment of a chemical moiety to a protein can significantly increase its circulation half-life (Jevsevar et al., *Biotechnol. J.*, 5: 113-128 (2010)). For molecular species with molecular weights below the glomerular filtration limit the conjugation of a large molecular weight moiety prevents renal clearance of the product. Also, addition of chemical moieties to pharmaceutical products can prevent receptor mediated removal of the molecule through steric hindrance.

The use of modifying molecules, such as biocompatible polymers to render the therapeutic agents more hydrophilic may also assist in the reduction or a prevention of an immune response to the introduced therapeutic agent. The modification provides a 'shield of water' around the agent, which may 'hide' any epitopes to which the immune system may otherwise respond. The presence of water molecules around the modified therapeutic agent may form a clathrate structure when in aqueous solution.

Furthermore, the use of the modification to allow subcutaneous delivery of the agent enables the gradual introduction of the therapeutic agent into the body via the lymphatic system, avoiding the reaction associated with bolus injections or intravenous infusion of large dosages, such as "red-man syndrome" associated with the intravenous administration of certain antibiotics.

Thus, many advantages can be envisaged by modifying such therapeutic agents for subcutaneous delivery and thereby subsequent infusion into the vascular system via the lymphatic system.

Accordingly, the present invention provides, as a first aspect a method of administering a therapeutic agent to a patient, comprising subcutaneously administering the therapeutic agent to the patient, such that the $C_{max}:C_{average}$ ratio is lower than the $C_{max}:C_{average}$ ratio of the agent when delivered intravenously, and wherein the agent is modified in order to increase the hydrophilicity and modify the molecular dimensions in relation to the native state of the therapeutic agent. The subcutaneous administration is such that the agent is at a more consistent concentration in the patient's bloodstream during the treatment period when compared to intravenous administration, which enables the $C_{max}:C_{average}$ ratio to be reduced.

Also provided is a method of administering a therapeutic agent to the lymphatic system of a patient, comprising the step of subcutaneously administering the therapeutic agent, such that it does not directly enter the circulatory system of the patient at the site of injection, and wherein the agent is modified in order to increase the hydrophilicity and modify the molecular dimensions in relation to the native state of the therapeutic agent, such that the modified agent is unable to enter the circulation directly from the site of administration.

Further provided is a method of preventing entry of a therapeutic agent directly into the local circulatory system of a patient upon subcutaneous administration of the therapeutic agent to a patient, the method comprising the step of subcutaneously administering the modified agent to the patient and wherein the agent is modified in order to increase the hydrophilicity and modify the molecular dimensions in relation to the native state of the therapeutic agent.

The subcutaneous administration of the modified agent enables a higher dose of the agent to be administered to the patient than by intravenous bolus injection; the patient to be re-dosed earlier than if the modified agent is administered intravenously; a lesser or equivalent immunogenic response than the intravenous administration of the modified agent to be achieved; provides a therapeutic benefit to the patient for a duration of at least 12 hours longer than the therapeutic benefit of the modified agent when administered intravenously; and the agent is deliverable at a concentration higher than the concentration of the modified agent that can be safely delivered intravenously.

The hydrophilicity is increased by at least the ratio of the molecular dimensions of the modified agent to the molecular dimensions of the unmodified agent. By hydrophilicity it is meant the hydrophilic to lipophilic balance (HLB), which may be defined as the affinity for water which in the context of this invention implies a lower capacity for surface adhesion and a higher dispersion in water.

The methods of the invention provide for modulating the speed of delivery of a therapeutic agent from a subcutaneous depot in a subject, comprising modifying the therapeutic agent to alter the hydrophilicity of the agent, wherein the level of hydrophilicity is proportional to the level of bioavailability.

It has been surprisingly found that to achieve the longest duration of depot release from the subcutaneous space, a lesser degree of modification is required. Without being bound by theory, this can be rationalised by the lesser degree of modification exposing some of the therapeutic agent to the subcutaneous tissue which confers a slow rate on the diffusion through the lymph. By contrast the higher degree of modification covers the therapeutic agent completely leaving the product free to quickly enter the blood circulation.

It has also been shown that the bioavailability favours the therapeutic agents which have been more highly modified, namely di- or tri-modified species compared to mono-modified species. The present inventors have therefore confirmed that the higher degrees of modification and hydration levels promote a higher degree of mobility and therefore bioavailability.

Consequently, for any given therapeutic agent the release from a subcutaneous depot can now be modulated by increasing or decreasing the level of modification of the therapeutic agent.

In accordance with the invention, subcutaneous delivery may be by subcutaneous injection, topical application, transdermal patch, microdermal abrasion, high pressure dry powder delivery, or any other method for introducing a therapeutic to the subcutaneous space.

A further aspect of the invention provides a modified agent comprising a therapeutic agent and a modification, wherein the modification increases the hydrophilicity and modifies the molecular dimensions of the agent in relation to the native state of the therapeutic agent for use in a method according to the first and further aspects. Modification of the agent may increase the hydrophilicity by at least 50% and the molecular dimensions by at least 50% of the agent in relation to the native state of the therapeutic agent.

An example of a biocompatible polymer which has been used in several marketed biopharmaceutical products is polyethylene glycol (herein referred to as PEG). The process of covalently attaching a PEG molecule to another molecule is termed PEGylation. To date, nine PEGylated products have received FDA market approval, with four being blockbuster drugs: PegIntron® (Schering-Plough), Pegasys® (Hoffman-La Roche), Neulasta® (Amgen) and Micera® (Hoffman-La Roche). A number of different chemistries have been used to conjugate protein therapeutics to activated PEG molecules. Random PEGylation has been used successfully to covalently link PEG moieties to proteins through amino groups on proteins. The attachment sites have most frequently, but not exclusively, been the ε-amino group on the side chains of lysine residues. Such random reactions can produce very complex mixtures of conjugates varying in the number and site of PEG moiety attachment. Even following purification of random conjugation reactions, positional isomers can be present which demonstrate very different physicochemical and pharmaceutical characteristics. A number of site-specific PEGylation techniques have been developed and are now being exploited to produce better defined biopharmaceuticals. Approaches taken to render site-specific PEGylation include N-terminal, cysteine, glycan, disulphide and poly-histidine targeted PEGylation.

The use of PEG to derivatize peptide therapeutics has been demonstrated to reduce the immunogenicity of the peptides. For example, U.S. Pat. No. 4,179,337 discloses non-immunogenic polypeptides such as enzymes and peptide hormones coupled to polyethylene glycol (PEG) or polypropylene glycol. In addition to reduced immunogenicity, the clearance time in circulation is prolonged due to the increased size of the PEG-conjugate of the polypeptides in question.

The principal mode of attachment of PEG, and its derivatives, to peptides is a non-specific bonding through a peptide amino acid residue (see U.S. Pat. Nos. 4,088,538, 4,496,689, 4,414,147, 4,055,635, and WO 87/00056). Another mode of attaching PEG to peptides is through the non-specific oxidation of glycosyl residues on a glycopeptide (see WO 94/05332).

In these non-specific methods, polyethyleneglycol is added in a random, non-specific manner to reactive residues on a peptide backbone. Of course, random addition of PEG molecules has its drawbacks, including a lack of homogeneity of the final product, and the possibility for reduction in the biological or enzymatic activity of the peptide. Therefore, for the production of therapeutic peptides, a derivitization strategy that results in the formation of a specifically labelled, readily characterizable, essentially homogeneous product is superior.

The state of the art in PEGylation of therapeutic agents, such as recombinant blood clotting factors, such as FVIIa, FVIII and FIX can be summarised as follows. WO 98/32466 suggests that FVII may be PEGylated, but does not contain any further information on the subject. US 2008/0200651 suggests that FVII polypeptides with wild-type, or increased, activity which have a PEG molecule conjugated via an artificially introduced cysteine residue demonstrate increased in vivo half-life. US 2008/0221032 describes the production of a FVIIa-polysialic acid conjugate which resulted in the molecule demonstrating a significantly increased in vivo half-life. US 2009/0176967 teaches that enzymes can be used to introduce specific functional groups at the C-terminus of the FVII polypeptide to which biocompatible polymers such as PEG can be coupled. US 2009/0227504 describes preparations of FVIIa (or FVIIa-like molecules) where one, or more, asparagine- and/or serine-linked oligosaccharide chains are covalently modified with at least one polymeric group which demonstrate improved serum half-life. US 2010/0028939 describes how natural glycoproteins can be modified using the enzyme galactose oxidase to produce reactive aldehyde functionalities on the glycan termini. The reactive aldehydes can then be used to conjugate polymeric moieties to the protein producing a product with improved pharmacological characteristics. US 2010/0056428 suggests that improved pharmacokinetic characteristics can be achieved in FVIIa by the derivitization of the glycoprotein by an oxime of a polymeric moiety such as PEG at a glycosyl group. Corresponding reports have been published in relation to FVIII and FIX, see US 2008/0255026 and U.S. Pat. No. 7,683,158 respectively.

Another approach to PEGylation of proteins has been developed by Polytherics and is known as TheraPEG™ in which a PEG polymer is attached to the protein of interest via a reduced disulphide bond of a pair of cysteine residues in the protein (WO 2005/007197). The technique has been used to prepare a PEGylated version of Factor IX free of contamination from Factor FIXa (WO 2009/130602), PEGylated Factor VII (WO 2011/135308) and PEGylated Factor VIII (WO 2011/135307).

It has now been discovered by the present inventors that subcutaneous administration of modified therapeutic agents such as PEGylated forms of blood clotting factors can result in improved half-lives and prolonged activity in plasma compared to equivalent forms delivered by intravenous administration, particularly when "dose adjusted". The specific location at which the subcutaneous injection is given may either increase or decrease the onset time in which the modified agent appears in the blood system. In any event, a lower $C_{max}:C_{average}$ ratio is achieved; similar pharmacokinetic profiles are seen usually associated with sustained release formulations and the like. The disadvantage with administering unmodified therapeutic agents subcutaneously is that they are able to enter directly into the cardiovascular system, and thereby the resultant $C_{max}$ and duration depends largely on the vascular condition of the site of subcutaneous injection. A highly vascularised region will clearly take up more quickly an amount of agent when administered by a subcutaneous injection into that area than an injection into a less vascularised area. Such inconsistencies may be overcome with the use of the modified agents of the invention for subcutaneous delivery.

The provision of a modified therapeutic agent in accordance with the present invention results in a molecule being delivered to the cardiovascular system via the lymph system and therefore is independent of the vasculature at the site of injection, leading to a more predictable, consistent rate of delivery into the circulation, via the lymphatic system.

Prior speculation in the art about formulations of therapeutic agents, including blood clotting factors, does not appreciate the advantages that could be derived from formulating such factors for subcutaneous administration. In particular, there is no hint or suggestion that such formulations when administered subcutaneously could deliver and maintain normal haemostasis for prolonged periods of time or that they could deliver a steadier level of drug bioavailability (lower $C_{max}:C_{average}$ ratio), which is due to the steady infusion effect achieved. The lymph system provides an aqueous fluid in which the vessel walls are collagen containing. Any molecule that is too big to go through blood vessel walls must rely on lymphatic drainage to reach to the bloodstream. However, if a degree of hydrophobic character exists in the molecule, it is likely to adhere to tissue both before it enters the lymph system and to the lymph vessel walls and will, thus, be immobile in the fluid. By contrast when a hydrophilic moiety is provided, the modified agents will more readily disperse in the aqueous phase of the lymph and drain easily into the system to enter the bloodstream at the thoracic duct.

The therapeutic agent of any aspect may be small molecule, macromolecule, polymer and polypeptide, wherein a small molecule includes hypnotics and sedatives, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, psychic energizers, tranquilizers, respiratory drugs, anticonvulsants, muscle relaxants, anti-Parkinson agents (dopamine antagonists), cytokines, growth factors, anticancer agents, antithrombotic agents, antihypertensives, cardiovascular drugs, analgesics, anti-inflammatories, antianxiety drugs (anxiolytics), appetite suppressants, anti-migraine agents, muscle contractants, anti-infectives (antibiotics, antivirals, antifungals, vaccines) anti-arthritics, anti-malarials, anti-emetics, anepileptics, bronchodilators nutritional agents and supplements, growth supplements, anti-enteritis agents, vaccines, antibodies, diagnostic agents, and contrasting agents.

Examples of agents suitable for use in the invention include, but are not limited to, calcitonin, erythropoietin (EPO), ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha I, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiramycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above an antibiotic, a blood factor, a hormone, a growth factor, another therapeutic peptide or protein, or a monoclonal antibody or a small molecule. Suitably, the agent to be modified may be selected from the group consisting of Factor VII, Factor VIII, Factor IX, Factor X, Factor Xa, Factor XI, Factor VIIa, Factor V, Factor XIII, von Willebrand's Factor and Protein C. In some embodiments the blood coagulation factor is suitably Factor VII, Factor VIII or Factor IX.

The agent in accordance with the invention may be modified by any biocompatible polymer, such as polyethylene glycol (PEG), poly-phosphatidyl choline (PC), polypropylene glycol (PPG), copolymers of ethylene glycol and propylene glycol, polyethylene oxide (PEO), polyoxyethylated polyol, polyolefinic alcohol, polyhydroxyalkylmethacrylate, polysaccharides, poly α-hydroxy acid, polyvinyl alcohol, polyphosphosphasphazene, poly N-acryloylmorpholine, polyalkyene oxide polymers, polymaleic acid, poly DL-alanine, carboxymethylcellulose, dextran, starch or starch derivatives, hyaluronic acid, chitin, polymethacrylates, polysialic acid (PSA), polyhydroxy alkanoates, poly amino acids and combinations thereof. The biocompatible polymer may have a linear or branched structure.

In a further embodiment, the biocompatible polymer is a protein selected from, but not limited to, the group consisting of albumin, transferrin, immunoglobulins including monoclonal antibodies, antibody fragments for example; single-domain antibodies, $V_L$, $V_H$, Fab, F(ab')$_2$, Fab', Fab3, scFv, di-scFv, sdAb, Fc and combinations thereof.

In some embodiments the increased hydrophilicity/solubility of the modified therapeutic agent delivered subcutaneously enables that agent to be constituted in a higher concentration in a delivery medium than if delivered intravenously. In the case where the drug product is administered by injection, this may enable a smaller injection volume to be used, which is more suitable to subcutaneous administration. In addition, at higher concentrations, where an unmodified agent might be expected to auto-catalyze, the modification prevents the agent from auto-digestion, which in the unmodified form might have led to undesirable, dangerous by-products. For example, unmodified blood factor IX will auto-catalyze at high concentrations to produce factor IXa, which is dangerously thrombogenic.

Accordingly, in another aspect of the present invention, the subcutaneous delivery volume of the modified therapeutic agent is no more than 2 ml. Suitably, the delivery volume may be 5 µl, 10 µl, 25 µl, 50 µl, 100 µl, 250 µl, 500 µl, 750 µl, or 1 ml. In alternative embodiments the delivery volume of the agent may be no more than 1.5 ml, 2 ml, 2.5 ml, 3.0 ml or 3.5 ml. It is important to note that the present invention allows for a higher concentration of an active agent to be delivered in a single subcutaneous injection more safely than by intravenous injection, since it is not delivered directly into the bloodstream of the patient. This is particularly important when dealing with blood clotting factors, since high concentration of blood clotting factors administered intravenously can result in undesirable and dangerous blood clots in the patient. Subcutaneous delivery allows the steady infusion of the active agent into the blood stream via the lymphatic system, thus avoiding the effect of dangerous levels of an active agent being delivered directly into the blood system. Therefore, since the concentration of delivery of the agent into the blood stream is regulated by the lymph system of the patient, a higher concentration may be delivered in a subcutaneous administration dose, which allows for smaller volumes to be used than traditionally used with intravenous delivery.

Within the scope of the present invention is included therapeutic agents that are able to be modified by hydrophilic modification to increase hydrophilicity and modify molecular dimensions in order to prevent direct entry into the vascular system through the blood vessel walls and that are administrable to the patient via subcutaneous delivery, in order to reach the circulatory system via the lymphatic system. Methods of modifying such agents are also included in the invention.

The dosage forms of the invention may be for administration at least once per day, at least twice per day, about once per week, about twice per week, about once per two weeks, or about once per month. The ability to modulate the release rate of the modified therapeutic agent from the subcutaneous depot means that the administration may be controlled more conveniently.

For certain therapeutic substances, a dosage regime of once per day will be sufficient, but for others a more frequent dosage regime may be more appropriate or desirable, where the amount delivered in each dosage administered subcutaneously may be reduced relative to a standard intravenous dosage. So for example a dosage form of the invention may be administered once per day, twice per day (or more if required).

The present invention allows the prevention of the rapid rise and subsequent fall (i.e. a "sawtooth") in the concentration of an agent in the blood. The present invention provides a more consistent, predictable concentration of the agent in the blood of a patient over a longer period of time than is traditionally seen with unmodified agents or the same modified product when repeatedly delivered intravenously.

A further benefit of the present invention is that it enables a higher dose of the agent to be administered subcutaneously than may be safely administered intravenously. This results in the provision of a longer duration of the therapeutic benefit than could ordinarily and safely be achieved by higher dosing or more frequent dosing via intravenous delivery. For example, in the case of blood factors, because the products are being delivered via the thoracic duct into the subclavian vein, the method enables a larger amount of product to be administered at a single time point as a single dose subcutaneously than could be administered at a single time point intravenously into a vein. Delivery of a high dose bolus into a vein may cause an undesirable thrombotic event.

A further benefit of the present invention enables the agent to be re-dosed at intervals to allow blood concentration of the agent to be maintained at a consistent level, providing a sustained constant and predictable therapeutic effect without the need to wait to re-dose until the concentration of the agent in the blood falls to therapeutically irrelevant levels. In traditional practice, intravenous re-dosing, with its immediate $C_{max}$ and onset of action, is delayed until it has been estimated that the level of the therapeutic has dropped to a level at which the addition of the $C_{max}$ from the new injection will not reach a potentially thrombogenic level (i.e. reducing the risk of an adverse event), but which means that the patient has reached an "unhealthy" range of a level of an agent in his or her bloodstream. In other words, subsequent doses of an agent are not normally given to the patient while "healthy levels", or therapeutically effective levels, of the agent are still present in the bloodstream. However, the present invention enables re-dosing of the agent to occur while blood levels of the agent are still in a therapeutic effective range, thus the invention provides for a more consistent therapeutic level of protein in the bloodstream, that is more ideally suited to prophylaxis. Due to the consistent delivery of the agent into the bloodstream via the thoracic duct, the problem of increasing the agent in the bloodstream to undesirably high levels is avoided.

According to an aspect of the invention, there is provided a dosage form of a pharmaceutical composition of a modified blood coagulation factor for subcutaneous administration which when formulated for subcutaneous administration to a subject provides a no more than once per month dosage form sufficient to maintain a whole blood clotting time in said subject of no more than 20 minutes. Also provided is a liquid dosage form of a PEGylated blood coagulation factor for subcutaneous administration no more than once per month wherein the dosage form has a $C_{max}$ of at least 10% and no more than 90% compared to an equivalent reference dosage form when administered intravenously, for use in the treatment of a blood clotting disorder. Suitably, the $C_{max}$ is from 20% to 80%, or from 30% to 70%, or from 40% to 60%. Suitably, the blood coagulation factor may be FVII, FVIII, or FIX.

By "no more than" it is meant that the dosage form may be administered more frequently than the time period specified, but it is not necessary to do so; the effect of the sub-cutaneous administration of such a dosage form means that the effects are seen for the duration of the time period. However, due to the lower and consistent $C_{max}$, more frequent dosing may occur without adverse effects to the patient.

Suitably, the dosage form of a blood clotting factor may be sufficient to maintain a whole blood clotting time in said subject of less than 15 minutes, or suitably, less than 12 minutes. In an embodiment, the dosage form of a blood clotting factor is an at least once per week dosage form, or at least once per month, at least once per two weeks, at least once per half week dosage form.

A dosage form according to the invention may comprise a blood clotting factor selected from the group consisting of Factor VIIa, Factor VII, Factor VIII, Factor IX, Factor X, Factor Xa, Factor XI, Factor XIII, Factor V, von Willebrand's Factor and Protein C. Suitably, the blood clotting factor may be FVII, FVIII, or FIX.

The dosage form of the invention may be modified by any biocompatible polymer, as defined herein. Suitably, the modification is PEGylation.

The dosage form may have a $C_{max}$ of at least 10% and no more than 90% compared to an equivalent reference dosage form when administered intravenously. In particular embodiments, the dosage form may have a $C_{max}$ of from 10% to 25% compared to an equivalent reference dosage form when administered intravenously. In particular embodiments, the dosage form may have a $C_{max}$ of from 40% to 60% compared to an equivalent reference dosage form when administered intravenously. In particular embodiments, the dosage form may have a $C_{max}$ of from 75% to 80% compared to an equivalent reference dosage form when administered intravenously. In particular embodiments, the dosage form may have a $C_{max}$ of 75% or of 78.8% compared to an equivalent reference dosage form when administered intravenously. In one embodiment, $C_{max}$ is 75 to 80% and the blood factor may be FVII. In another embodiment $C_{max}$ is 10% to 25% and the blood factor may be FVIII. In yet another embodiment $C_{max}$ is 40% to 60% and the blood factor may be FIX.

Also provided is a dosage formulation according to the invention, in which the dosage is of from 1 to 1000 IU/kg, or from 5 to 500 IU/kg, or from 100 to 250 IU/kg or from 25 to 50 IU/kg.

The dosage form of the present invention allows for a less frequent dosing of the dosage form, which is still sufficient to maintain the whole blood clotting time in a subject of no more than 20 minutes, or no more than 15 minutes, or no more than 10 minutes. In one embodiment, the dosage form is sufficient to maintain whole blood clotting time of less than 12 minutes. The dosage form may provide a no more than once a fortnight, no more than once a week, no more than twice a week, no more than once every three days, no more than once every 2 days, no more than once a day or a more or less frequent dosage form.

It is important to note that one benefit of the present invention is that the dosage form when the agent is a blood clotting factor, does not need to be administered to the patient more frequently than these intervals in order to continue to maintain whole blood clotting time in a healthy range, but it may be administered more frequently in order to help to provide a "steady state" similar to that of a controlled release formulation. A 'normal' whole blood clotting time is generally considered by one skilled in the art to be 10 to 12 minutes, and anything under 15 minutes is considered to be healthy in a non-haemophiliac human. Once whole blood clotting time is over 20 minutes, it is considered to be in an unhealthy range. Between 15 and 20 minutes is considered to indicate that although bleeding is under control, it is not normal.

In another embodiment the dosage form is administered less frequently than would be predicted by the plasma half life of a bolus intravenous injection. For example, a bolus injection of modified Factor IX may be required once a week, whereas the same agent delivered subcutaneously in accordance with the invention, may only be required once per ten days, or less.

According to a further aspect of the invention, there is provided a dosage form of a pharmaceutical composition of 25 to 50 IU/kg of a modified blood coagulation factor for subcutaneous administration at the same or with less frequency than the blood coagulation factor administered intravenously.

Formulations of the present invention are therefore able to maintain a normal value for haemostasis of up to seven days in which a normal value is defined as a Whole Blood Clotting Time (WBCT) of less than 15 minutes, suitably, about 12 minutes or less.

The formulations of the invention have a $C_{max}$ of at least 10%, to no more than 90% compared to an equivalent reference dosage form when administered intravenously. In some embodiments of the invention, the value may be at least 75%, 78% or 80%, and the blood factor may be FVII. In some embodiments of the invention, the value may be at least 15%, 18% or 20% and the blood factor may be FVIII. In some embodiments of the invention the value may be 40%, 45% or 50% and the blood factor may be FIX.

The formulations of specific embodiments of the invention wherein the modified agent is a PEGylated blood factor when formulated for subcutaneous administration no more than once per month comprise a dosage of from 25 to 50 IU/kg. In some embodiments the dosage may be 25, 30, 35, 40, 45, or 50 IU/kg. The dosage may be from 25 IU/Kg to 30 IU/Kg, 35 IU/Kg to 40 IU/Kg, or 40 IU/Kg to 50 IU/Kg.

In one embodiment, when the dosage form is prepared as a dose of 150 IU/Kg, the formulation may be suitable for administration once every two weeks to a subject in need thereof. Suitably, the formulation may be for administration no more than once every two weeks.

According to an embodiment of the invention, a dosage form of a modified blood coagulation factor when formulated for subcutaneous administration can result in normal haemostasis being maintained for at least one half of a week.

Dosage forms in accordance with the invention, when administered subcutaneously result in lower amounts of the modified blood coagulation (clotting) factor being required to achieve the same therapeutic end-point thus providing safer products for subjects in need of treatment. In one embodiment half the adjusted dose of modified blood clotting factor administered intravenously is sufficient to achieve normal haemostasis for at least one week in subjects, particularly wherein the blood coagulation factor is Factor VIIa or Factor VIII. A suitable value for normal haemostasis is a Whole Blood Clotting Time (WBCT) of about 12 minutes, as described above.

Formulations of the invention may suitably comprise less than half the dose adjusted therapeutically effective amount of a reference formulation formulated for intravenous administration comprising the same modified blood coagulation factor in order to achieve the same therapeutic effect. For example, in an embodiment wherein the blood coagulation factor is Factor IX.

The invention therefore also provides for a dosage form of a modified blood coagulation factor for subcutaneous administration in which the dosage form comprises 50% of the dose adjusted amount required for intravenous administration in order to achieve the same duration of effective action.

A formulation suitable for subcutaneous administration may suitably be prepared as an aqueous or substantially aqueous formulation. The formulation may comprise such additional salts, preservatives and stabilisers and/or excipients or adjuvants as required. The dosage forms of the invention may be provided as anhydrous powders ready for extemporaneous formulation in a suitable aqueous medium.

It may be generally preferred to formulate such dosage forms as a buffered aqueous formulation. Suitable buffer solutions may include, but are not limited to amino acids (for example histidine), salts of inorganic acids and alkali metals or alkaline earth metals, (for example sodium salts, magnesium salts, potassium salts, lithium salts or calcium salts— exemplified as sodium chloride, sodium phosphate). Other components such as detergents or emulsifiers (for example, Tween 80® or any other form of Tween®) may be present and stabilisers (for example benzamidine or a benzamidine derivative). Excipients such as sugars, (for example sucrose) may also be present. Suitable values for pH are physiological pH, e.g. pH 6.8 to 7.4. Liquid dosage forms may be prepared ready for use in such administration vehicles.

A "modified blood coagulation factor" is a blood coagulation factor (blood clotting factor) which has been linked to one or more modifying agents as described above. In some embodiments, the modification is PEG. The PEG molecule may be linked directly or indirectly to the blood coagulation factor. The PEGylated blood coagulation factor can also be defined as a "blood coagulation factor conjugated to a PEG molecule" or a "blood coagulation factor-PEG conjugate".

Modified blood coagulation factors (blood clotting factors) suitably comprise at least one of Factor VII, Factor VIII, Factor IX, Factor X, Factor Xa, Factor XI, Factor VIIa, Factor V, Factor XIII, von Willebrand's Factor and Protein C. In some embodiments the blood coagulation factor is suitably Factor VII, Factor VIII or Factor IX.

As used herein, the term "blood factor conjugate" refers to a blood clotting factor protein that has been modified to include a modification, such as a PEG moiety, other conjugated moiety as defined above.

The terms Factor VIIa (FVIIa) and Factor VII (FVII) are also used interchangeably unless the context specifies otherwise. FVIII is used as an abbreviation for Factor VIII and FIX is used as an abbreviation for Factor IX, and so on for blood factors described herein.

The blood coagulation (clotting) factor may be from any suitable source and may be a recombinant protein produced by recombinant DNA technology using molecular biological techniques or synthesised chemically or produced transgenically in the milk of a mammal, or the factor may be isolated from natural sources (e.g. purified from blood plasma). Suitably the factor is a mammalian blood clotting factor, such as a human blood clotting factor. References to a blood clotting factor include a blood coagulation factor.

As indicated herein the present invention relates to formulations of blood clotting factors which have been modified by conjugation with one or more modifying agents, such as polyethylene glycol polymers ("PEGylation"). The modification of the blood clotting factor may be by any convenient means.

Tween® is currently extensively used in the formulation of blood products. Tween® 80 is a PEGylated fatty acid which carries a molecular weight equivalent of PEG of approximately 0.8 kilo Daltons per Tween® molecule.

As discussed above, blood factors are all characterised inter alia by the property of surface adhesion. This is a necessary feature of the coagulation cascade which requires that enzymes and cofactors adhere to other participants in the cascade, to the surface of platelets and to tissue at the site of injury. Indeed it is particularly important that a blood clot remains at the site of injury and does not drift to cause a dangerous thrombosis. This property presents a challenge in the formulation of drug products, since blood factors such as VIIa VIII and IX will adhere excessively to any glass and plastic surfaces. In practical terms this is mitigated by the extensive use of polysorbate (e.g. Tween® 80).

In one embodiment of the present invention, FVIII has a 20 kDa straight chain polyethylene glycol moiety conjugated to it. The conjugation of PEG mitigates the surface adhesion property of this factor to the extent that no further use of Tween® is necessary.

When activated in the process of coagulation, PEG-FVIII still adheres to the surface of platelets and is a small component in the overall clotting process. In this regard, blood clots will form in the normal manner on platelets at the site of injury.

By having a mono-PEGylated factor and thereby obviating the requirement for additional Tween® in the formulation, a decrease in the amount of polyethylene glycol can be achieved. A calculation using Kogenate® FS (Bayer FVIII) was performed to identify the total amount of PEG per mol of FVIII used in the formulation and make a comparison to a single conjugated 20 kDa moiety which does not require any further Tween® in its formulation. Thus, on a dose-for-dose basis, an embodiment of the present invention provides a 25.8 fold reduction in polyethylene glycol, which, when the reduced frequency of dosing is also taken into account, may result in an overall reduction in the administration of PEG of approximately 80-fold.

The present inventors have found that increasing the water-carrying capability of the target therapeutic (for example via di-PEGylating a product versus mono-PEGylating it), the passage of the product into the bloodstream, following subcutaneous administration, can be accelerated. Conversely, decreasing the water-carrying capability (for example mono-PEGylating the products versus di-PEGylating it), the passage of the product into the bloodstream, following subcutaneous administration, can be slowed, giving a depot effect. Without wishing to be bound by theory, it would appear that the same product with a lesser water-carrying ability (e.g. via mono-PEGylation or with a smaller PEG molecule) resists being dispersed through the subcutaneous space for longer than the same product modified to have a greater water-carrying capability (e.g. via multi-PEGylation or the attachment of a larger PEG molecule), thus providing the enhanced depot effect.

Without wishing to be bound by theory, designing a product to have a greater water carrying characteristic (for example by increasing its PEG coverage via di- or multi-PEGylation, increasing the size of the PEG or using branched vs. straight PEG molecules) would seem to render it more water dispersible within the subcutaneous space, leading to a faster rate of entry via the lymphatic vessels into the plasma; the reduced hydrophilicity of products designed to have a lesser water-carrying characteristic (for example via mono-PEGylation or via the use of smaller PEG molecules), would seem to leave more of the hydrophobic therapeutic agent exposed reducing its dispersibility and slowing its entry into the plasma via the aqueous lymphatic system.

This ability to modify the dispersion characteristics of a molecule for sub-cutaneous administration, by selectively adjusting the balance between hydrophilicity and hydrophobicity, provides an exquisite degree of control over the controlled release of a product from the subcutaneous space to the plasma via the lymph, which may be adjusted according to the characteristics of the therapeutic agent, the needs and physiology of the patient or a combination of these or other influencing factors.

In some embodiments, when the modification is PEG, the polyethylene glycol (PEG) may have a linear or branched structure and may be attached to the therapeutic agent via any convenient route. Where the therapeutic agent is a protein, e.g. a blood clotting factor or other therapeutic protein as described herein, conjugation of PEG may be via a serine or threonine residue in the native protein, via a hydroxyl residue on a sugar residue attached to the native protein, or via one or more cysteine residues. The PEG moiety may be attached via such residues which occur in the native or the recombinant forms of the protein. Proteins made by recombinant expression allow for site specific engineering to insert desired amino acid residues into a protein sequence and/or to control patterns of glycosylation with specific glycosylase enzymes. Other routes for PEGylation include amide or N-terminal amino group PEGylation, or carboxyl group PEGylation.

The PEG moiety may also be conjugated to the blood clotting factor, i.e. Factor VII, Factor VIII, Factor IX, Factor X, Factor Xa, Factor XI, Factor VIIa, Factor V, Factor XIII, von Willebrand's Factor or Protein C, via one or more reduced cysteine disulphide bonds. A free cysteine residue is the result of reducing a cystine disulphide bond in the protein. For example, the conjugation may be by means of a linker group bridging the sulphur residues of two cysteine residues that formed a disulphide bond in Factor VII, Factor VIII, Factor IX, Factor X, Factor Xa, Factor XI, Factor VIIa, Factor V, Factor XIII, von Willebrand's Factor or Protein C. The disulphide bond may therefore be a native disulphide bond or a recombinantly introduced disulphide bond.

In one embodiment of the invention, the hydrophilic moiety, such as the polyethylene glycol chain is attached via a bivalent linker moiety across two cysteine residues that normally form a disulphide bridge in the native form of the blood clotting factor.

The PEG molecule may be of any suitable molecular weight, for example from 1 kDa to 100 kDa, 10 to 500 kDa, suitably 5 to 30 kDa or 20 to 30 kDa. Some suitable molecular weights include 5, 10, 20, or 30 kDa. Suitably, the PEG molecule may be from 5 kDa to 40 kDa.

There are several different types of polyethylene glycol polymers that will form conjugates with Factor VII, Factor VIII, Factor IX, Factor X, Factor Xa, Factor XI, Factor VIIa, Factor V, Factor XIII, von Willebrand's Factor or Protein C. There are linear PEG polymers that contain a single polyethylene glycol chain, and there are branched or multi-arm PEG polymers. Branched polyethylene glycol contains 2 or more separate linear PEG chains bound together through a unifying group. For example, two PEG polymers may be bound together by a lysine residue. One linear PEG chain is bound to the α-amino group, while the other PEG chain is bound to the ε-amino group. The remaining carboxyl group of the lysine core is left available for covalent attachment to a protein. Both linear and branched polyethylene glycol polymers are commercially available in a range of molecular weights.

In one embodiment of the invention, the Factor VII, Factor VIII, Factor IX, Factor X, Factor Xa, Factor XI, Factor VIIa, Factor V, Factor XIII, von Willebrand's Factor or Protein C—conjugate contains one or more linear polyethylene glycol polymers bound to Factor VII, Factor VIII, Factor IX, Factor X, Factor Xa, Factor XI, Factor VIIa, Factor V, Factor XIII, von Willebrand's Factor and Protein C. In some embodiments the blood coagulation factor is Factor III, Factor VIII or Factor IX, in which each PEG has a molecular weight between about 2 kDa to about 100 kDa. In another aspect of the invention, a Factor VII, Factor VIII, Factor IX, Factor X, Factor Xa, Factor XI, Factor VIIa, Factor V, Factor XIII, von Willebrand's Factor or Protein C-conjugate contains one or more linear polyethylene glycol polymers bound to Factor VII, Factor VIII, Factor IX, Factor X, Factor Xa, Factor XI, Factor VIIa, Factor V, Factor XIII, von Willebrand's Factor or Protein C, wherein each linear PEG has a molecular weight between about 1 kDa to about 40 kDa. In certain embodiments, each linear PEG has a molecular weight between about 10 kDa to about 30 kDa. In certain embodiments, each linear PEG has a molecular weight that is about 20 kDa. In certain embodiments, each linear PEG has a molecular weight that is about 10 kDa. In certain embodiments, each linear PEG has a molecular weight that is less than 10 kDa. In particular embodiments, where the blood factor conjugate contains more than one linear PEG polymers bound to a blood coagulation factor, for example two, three, or up to eight linear PEG polymers bound to Factor VII, Factor VIII, Factor IX, Factor X, Factor Xa, Factor XI, Factor VIIa, Factor V, Factor XIII, von Willebrand's Factor or Protein C. In some embodiments, the blood factor conjugates contain multiple linear PEG polymers, where each linear PEG has a molecular weight of about 5-30 kDa.

A blood factor conjugate of this invention may contain one or more branched PEG polymers bound to Factor VII, Factor VIII, Factor IX, Factor X, Factor Xa, Factor XI, Factor VIIa, Factor V, Factor XIII, von Willebrand's Factor or Protein C, wherein each branched PEG has a molecular weight between about 2 kDa to about 100 kDa. In another aspect of the invention, a blood factor conjugate contains one or more branched polyethylene glycol polymers bound to Factor VII, Factor VIII, Factor IX, Factor X, Factor Xa, Factor XI, Factor VIIa, Factor V, Factor XIII, von Willebrand's Factor or Protein C, wherein each branched PEG has a molecular weight between about 1 kDa to about 100 kDa. In certain embodiments, each branched PEG has a molecular weight between about 5 kDa to about 40 kDa. In certain embodiments, each branched PEG has a molecular weight that is about 10 kDa, 20 kDa, or about 30 kDa. In certain embodiments, each branched PEG has a molecular weight that is less than about 10 kDa. In particular embodiments, where the blood factor conjugate contains more than one branched PEG polymers bound to Factor VII, Factor VIII, Factor IX, Factor X, Factor Xa, Factor XI, Factor VIIa, Factor V, Factor XIII, von Willebrand's Factor or Protein C, for example two, three, or up to eight branched PEG polymers bound to Factor VII, Factor VIII, Factor IX, Factor X, Factor Xa, Factor XI, Factor VIIa, Factor V, Factor XIII, von Willebrand's Factor or Protein C. In a some embodiments, the Factor VII, Factor VIII, Factor IX, Factor X, Factor Xa, Factor XI, Factor VIIa, Factor V, Factor XIII, von Willebrand's Factor or ProteinC-PEG conjugates contains up to eight branched PEG polymers, where each branched PEG has a molecular weight of about 5-40 kDa, suitably 10 to 30 kDa.

The blood factor-PEG conjugates may be purified by chromatographic methods known in the art, including, but not limited to ion exchange chromatography and size exclusion chromatography, affinity chromatography, precipitation and membrane-based separations.

Suitably, the PEG moiety of the Factor VII, Factor VIII, Factor IX, Factor X, Factor Xa, Factor XI, Factor VIIa, Factor V, Factor XIII, von Willebrand's Factor or Protein C-conjugate may be bound to two cysteine residues, which form a disulphide bond in the blood coagulation factor. Therefore, the PEG containing linker bridges the disulphide bond. Examples of such conjugation procedures are described in WO 2005/007197, WO 2009/047500 and WO 2010/010324.

As discussed above, other routes of PEGylation may include standard glycoPEGylation procedures as described in Stennicke et al (*Thromb. Haemost.* 2008, 100(5), 920-8), or N-terminal amide PEGylation as described in U.S. Pat. No. 5,644,029.

In one embodiment of the invention, a PEG moiety can be conjugated to Factor VII, Factor VIII, Factor IX, Factor X, Factor Xa, Factor XI, Factor VIIa, Factor V, Factor XIII, von Willebrand's Factor or Protein C according to the scheme set out in FIG. 2. In FIG. 2, a group R1 is shown between the PEG moiety and the linker group spanning the sulphur atoms of the disulphide bond on the blood factor molecule.

R1 represents a substituent which can be a direct bond, an alkylene group (preferably a $C_{1-10}$ alkylene group), or an optionally-substituted aryl or heteroaryl group; wherein the aryl groups include phenyl, benzoyl and naphthyl groups; wherein suitable heteroaryl groups include pyridine, pyrrole, furan, pyran, imidazole, pyrazole, oxazole, pyridazine, pyrimidine and purine; wherein linkage to the polymer may be by way of a hydrolytically labile bond, or by a non-labile bond.

Particular substituents which may be present on the optionally substituted aryl or heteroaryl group include for example one or more of the same or different substituents selected from —CN, —NO$_2$, —CO$_2$R, —COH, —CH$_2$OH, —COR, —OR, —OCOR, —OCO$_2$R, —SR, —SOR, —SO$_2$R, —NHCOR, —NRCOR, —NHCO$_2$R, —NR'CO$_2$R, —NO, —NHOH, —NR'OH, —C=N—NH-COR, —C=N—NR'COR, —N$^+$R$_3$, —N$^+$H$_3$, —N$^+$HR$_2$, —N$^+$H$_2$R, halogen, for example fluorine or chlorine, —C≡CR, —C=CR$_2$ and $^{13}$C=CHR, in which each R or R' independently represents a hydrogen atom or an alkyl (preferably $C_{1-6}$) or an aryl (preferably phenyl) group. The presence of electron withdrawing substituents is especially preferred. In one embodiment, the optionally-substituted aryl or heteroaryl group in R1 includes aryl or heteroaryl groups substituted by an amide (NHCO) group which connects the R1 unit to the PEG moiety.

The linker group between the two sulphur atoms of the original disulphide bond between the cysteine residues of Factor VII, Factor VIII, Factor IX, Factor X, Factor Xa, Factor XI, Factor VIIa, Factor V, Factor XIII, von Willebrand's Factor or Protein C may therefore comprise a 3-carbon bridge. In one embodiment, the linker group between the two sulphur atoms of the original disulphide bond between the cysteine residues of Factor VII, Factor VIII, Factor IX, Factor X, Factor Xa, Factor XI, Factor VIIa, Factor V, Factor XIII, von Willebrand's Factor or Protein C is $(CH_2)_2CHC(O)$—.

In one embodiment of the invention, the PEG moiety may be conjugated as described above wherein the composition comprising Factor VII, Factor VIII, Factor IX, Factor X, Factor Xa, Factor XI, Factor VIIa, Factor V, Factor XIII, von Willebrand's Factor or Protein C conjugated to a PEG moiety has the structure:

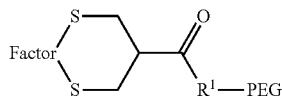

Where R1 is as defined above, and "Factor" represents a blood clotting factor.

In embodiments where the optionally-substituted aryl or heteroaryl group in R1 as defined above includes aryl or heteroaryl groups substituted by an amide (NHCO) group, the structure of the conjugate protein, where R3 is as defined below, may be as follows:

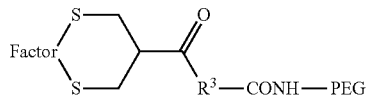

R3 represents a substituent which can be a direct bond, an alkylene group (preferably a $C_{1-10}$ alkylene group), or an optionally-substituted aryl or heteroaryl group; wherein the aryl groups include phenyl, benzoyl and naphthyl groups; wherein suitable heteroaryl groups include pyridine, pyrrole, furan, pyran, imidazole, pyrazole, oxazole, pyridazine, pyrimidine and purine; wherein linkage to the polymer may be by way of a hydrolytically labile bond, or by a non-labile bond, and "Factor" represents a blood clotting factor.

Particular substituents which may be present on the optionally substituted aryl or heteroaryl group include for example one or more of the same or different substituents selected from —CN, —NO₂, —CO₂R, —COH, —CH₂OH, —COR, —OR, —OCOR, —OCO₂R, —SR, —SOR, —SO₂R, —NHCOR, —NRCOR, —NHCO₂R, —NR'CO₂R, —NO, —NHOH, —NR'OH, —C═N—NH— COR, —C═N—NR'COR, —N⁺R₃, —N⁺H₃, —N⁺HR₂, —N⁺H₂R, halogen, for example fluorine or chlorine, —C≡CR, —C═CR₂ and ¹³C═CHR, in which each R or R' independently represents a hydrogen atom or an alkyl (preferably C1-6) or an aryl (preferably phenyl) group. The presence of electron withdrawing substituents is especially preferred.

In some embodiments, dosage forms of the present invention may be composed of PEGylated forms of blood clotting factors as defined herein in which the polyethyleneglycol molecule is a straight-chain, (suitably mono-disperse) form. The PEG may be conjugated to the blood clotting factor via a three carbon bridge moiety. For example, the PEG may be 1 to 100 kDa; in some embodiments, 5 to 30 kDa; in some embodiments 10 kDa and in other embodiments 20 kDa.

The dosage form may be prepared for subcutaneous administration by formulation in a suitable aqueous vehicle. In most embodiments, the suitable aqueous solution is buffered to physiological pH (for example to pH 6.8) with a composition comprising one or more amino acids and/or salts (for example histidine and NaCl) and in the presence of a non-ionic surfactant (for example Tween® 80) and optionally a stabiliser (for example benzamidine or a benzamidine derivative, see U.S. Pat. No. 7,612,066 for example).

Nonionic surfactants/emulsifiers which can be used according to the present invention include polysorbates such as polyoxyethylene sorbitan monooleate (polysorbate 80, Tween® 80), polysorbate 65, polysorbate 65, polysorbate 61, polysorbate 60, polysorbate 40, polysorbate 21, polysorbate 20, polysorbate 81, polysorbate 85, and polysorbate 120, and polyoxyethylene stearates such as polyoxyl 8 stearate (PEG 400 monostearate), polyoxyl 2 stearate, polyoxyl 4 stearate, polyoxyl 6 stearate, polyoxyl 12 stearate, polyoxyl 20 stearate, polyoxyl 30 stearate, polyoxyl 40 stearate, polyoxyl 50 stearate, polyoxyl 100 stearate, polyoxyl 150 stearate, and polyoxyl 4 distearate, polyoxyl 8 distearate, polyoxyl 12 distearate, polyoxyl 32 distearate, polyoxyl 150 distearate.

Suitable concentration ranges for the components in the composition may be for example 5 mM to 25 mM histidine (suitably 10 mM to 15 mM histidine), 10 mM to 50 mM NaCl (suitably 30 mM to 40 mM NaCl) and 0.001 to 0.01% Tween® 80 (suitably 0.005% to 0.008% Tween® 80) and optionally 0.5 mM to 5 mM benzamidine (suitably 1 mM to 2 mM benzamidine).

As used herein the term "muteins" refers to analogs of an Factor VII, Factor VIII, Factor IX, Factor X, Factor Xa, Factor XI, Factor VIIa, Factor V, Factor XIII, von Willebrand's Factor or Protein C, in which one or more of the amino acid residues of the naturally occurring components of Factor VII, Factor VIII, Factor IX, Factor X, Factor Xa, Factor XI, Factor VIIa, Factor V, Factor XIII, von Willebrand's Factor or Protein C are replaced by different amino acid residues, or are deleted, or one or more amino acid residues are added to the original sequence of a blood factor, without changing considerably the activity of the resulting products as compared with the original blood factor. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes an Factor VII, Factor VIII, Factor IX, Factor X, Factor Xa, Factor XI, Factor VIIa, Factor V, Factor XIII, von Willebrand's Factor or Protein C in accordance with the present invention, under stringent conditions. The term "stringent conditions" refers to hybridization and subsequent washing conditions, which those of ordinary skill in the art conventionally refer to as "stringent" (Ausubel et al., *Current Protocols in Molecular Biology*, Interscience, N.Y., sections 63 and 6.4 (1987, 1992); Sambrook et al. (Sambrook et al., *Molecular Cloning: A Laboratory Manual*, Cold Spring Harbor Laboratory Press, Cold Spring Harbor, N.Y. (1989)).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1.times.SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC.

Any such mutein preferably has a sequence of amino acids sufficiently duplicative of that of an Factor VII, Factor VIII, Factor IX, Factor X, Factor Xa, Factor XI, Factor VIIa, Factor V, Factor XIII, von Willebrand's Factor or Protein C such as to have substantially similar, or even better, activity to Factor VII, Factor VIII, Factor IX, Factor X, Factor Xa, Factor XI, Factor VIIa, Factor V, Factor XIII, von Willebrand's Factor or Protein C.

One characteristic activity of Factor VII, Factor VIII, Factor IX, Factor X, Factor Xa, Factor XI, Factor VIIa, Factor V, Factor XIII, von Willebrand's Factor or Protein C is its capability of participate in the blood coagulation cascade and assays to detect Factor VII, Factor VIII, Factor IX, Factor X, Factor Xa, Factor XI, Factor VIIa, Factor V, Factor XIII, von Willebrand's Factor or Protein C. As long as the mutein has substantial blood factor activity, it can be considered to have substantially similar activity to blood factor. Thus, it can be determined whether any given mutein has at least substantially the same activity as Factor VII, Factor VIII, Factor IX, Factor X, Factor Xa, Factor XI, Factor VIIa, Factor V, Factor XIII, von Willebrand's Factor or Protein C by means of routine experimentation comprising subjecting such a mutein to assays as described herein.

In a preferred embodiment, any such mutein has at least 40% identity or homology with the amino acid sequence of Factor VII, Factor VIII, Factor IX, Factor X, Factor Xa, Factor XI, Factor VIIa, Factor V, Factor XIII, von Willebrand's Factor or Protein C. More preferably, it has at least 50%, at least 60%, at least 70%, at least 80% or, most preferably, at least 90%, 95%, 98% or 99% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux, et al., Nucleic acids Research, 12: 387 (1984)), for example the programs BESTFIT and GAP, may be used to determine the percentage identity between two polynucleotides and the percentage identity and the percentage homology between two polypeptide sequences. BESTFIT uses the "local homology" algorithm of Smith and Waterman (Advances in Applied Mathematics, 2; 482-489 (1981)) and finds the best single region of similarity between two sequences. Other programs for determining identity and/or similarity between sequences are also known in the art, for instance the BLAST family of programs (Atschul et al., J. Molec. Biol., 215: 403 (1990), accessible through the home page of the NCBI, at www.ncbi.nlm.nih.gov) and FASTA (Pearson W R, Methods in Enzymology, 183: 63-98 (1990)).

Muteins of Factor VII, Factor VIII, Factor IX, Factor X, Factor Xa, Factor XI, Factor VIIa, Factor V, Factor XIII, von Willebrand's Factor or Protein C, which can be used in accordance with the present invention include a finite set of substantially corresponding sequences as substitution peptides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of Factor VII, Factor VIII, Factor IX, Factor X, Factor Xa, Factor XI, Factor VIIa, Factor V, Factor XIII, von Willebrand's Factor or Protein C, may include synonymous amino acids within a group which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the scope of the present invention.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

In addition fusion proteins comprising Factor VII, Factor VIII, Factor IX, Factor X, Factor Xa, Factor XI, Factor VIIa, Factor V, Factor XIII, von Willebrand's Factor or Protein C, fused with another peptide or protein fragment may be also be used provided that the fusion protein retains the activity of Factor VII, Factor VIII, Factor IX, Factor X, Factor Xa, Factor XI, Factor VIIa, Factor V, Factor XIII, von Willebrand's Factor or Protein C. The term "fusion protein" in this text means, in general terms, one or more proteins joined together by chemical means, including hydrogen bonds or salt bridges, or by peptide bonds through protein synthesis or both.

"Functional derivatives" as used herein cover derivatives of Factor VII, Factor VIII, Factor IX, Factor X, Factor Xa, Factor XI, Factor VIIa, Factor V, Factor XIII, von Willebrand's Factor or Protein C, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of blood factors, and do not confer toxic properties on compositions containing it.

These derivatives may, for example, include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties, including for example glycosylation of available hydroxyl residues.

An "active fragment of blood factor" according to the present invention may be a fragment of Factor VII, Factor VIII, Factor IX, Factor X, Factor Xa, Factor XI, Factor VIIa, Factor V, Factor XIII, von Willebrand's Factor or Protein C or a mutein as defined herein. The term fragment refers to any subset of the molecule, that is, a shorter peptide that retains the desired biological activity. Fragments may readily be prepared by removing amino acids from either end of the blood factor molecule and testing the resultant fragment for its properties as described herein. Proteases for removing one amino acid at a time from either the N-terminal or the C-terminal of a polypeptide are known, and so determining fragments, which retain the desired biological activity, involves only routine experimentation.

As active fractions of an Factor VII, Factor VIII, Factor IX, Factor X, Factor Xa, Factor XI, Factor VIIa, Factor V, Factor XIII, von Willebrand's Factor and Protein C, muteins and active fragments thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to Factor VII, Factor VIII, Factor IX, Factor X, Factor Xa, Factor XI, Factor VIIa, Factor V, Factor XIII, von Willebrand's Factor or Protein C.

The term "salts" herein refers to both salts of carboxyl groups and to acid addition salts of amino groups of the Factor VII, Factor VIII, Factor IX, Factor X, Factor Xa, Factor XI, Factor VIIa, Factor V, Factor XIII, von Willebrand's Factor or Protein C molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of blood factors as described herein.

The "area under the curve" or "AUC", as used herein in the context of administering a therapeutic agent to a patient, is defined as total area under the curve that describes the concentration of a drug in systemic circulation in the patient as a function of time from zero to infinity. As used herein the term "clearance" or "renal clearance" is defined as the volume of plasma that contains the amount of drug excreted per minute.

As used herein the term "half-life" or "t1/2", in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. The precise impact of PEGylation on alpha phase and beta phase half-lives will vary depending upon the size and other parameters, as is well known in the art. Further explanation of "half-life" is found in Pharmaceutical Biotechnology (1997, DFA Crommelin and RD Sindelar, eds., Harwood Publishers, Amsterdam, pp 101-120).

As used herein the term "residence time", in the context of administering a peptide drug to a patient, is defined as the average time that drug stays in the body of the patient after dosing.

As used herein the term "immunogenicity", in the context of administering a peptide drug to a patient, is defined as the propensity of that peptide drug to illicit an immune response in the patient after dosing, or after repeat dosing.

As used herein the term "molecular dimensions" means the weight, size and/or shape of an agent. Thus, "increasing the molecular dimensions by modification" means that the molecular dimensions are increased such that the agent is too large in physical size to pass through the blood vessel walls into the blood stream. The molecular dimensions, however do not necessarily mean an increase in molecular weight, if, for example, an agent is truncated prior to modification. Molecular dimensions may include molecular/ weight, size and/or conformation provide that the modified agent retains activity and cannot pass directly into the blood vessels without being delivered thereto by the lymphatic system.

As used herein, the term "subcutaneous delivery" or "subcutaneous administration" means delivery by any suitable means such that the therapeutic agent is delivered through the skin directly to the subcutaneous space.

As used herein, "dose adjusted" in the context of subcutaneous doses of the modified agent means the intravenous dose for the modified agent multiplied by the fraction intravenous $C_{max}$/subcutaneous $C_{max}$. As explained herein, the methods of the present invention allow for less frequent dosing and/or higher doses to be given to a patient when compared to the unmodified or modified agent administered intravenously. "Dose unadjusted" in the context of subcutaneous doses means the same dose of intravenous of the modified agent is delivered as would be delivered intravenously.

As used herein, the term "subcutaneous space" means the connective tissue under the skin. It excludes blood vessels, the blood stream and internal organs.

By "native state" it is meant the state in which an agent exists prior to modification and in the state in which it is generally intravenously administered to a patient in a pharmaceutically acceptable form.

The subcutaneous dosage forms of the invention may further comprise a pharmaceutically acceptable diluent, adjuvant or carrier. Subcutaneous dosage forms adapted for sub-cutaneous administration can include aqueous and/or non-aqueous sterile injection solution(s) which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

In general, the subcutaneous dosage forms may contain preserving agents, solubilising agents, stabilising agents, wetting agents, emulsifiers, colourants, salts (active substances of the present invention may themselves be provided in the form of a pharmaceutically acceptable salt), buffers, or antioxidants. They may also contain therapeutically active agents in addition to the substance of the present invention. The subcutaneous dosage forms of the invention may be employed in combination with pharmaceutically acceptable diluents, adjuvants, or carriers. Such excipients may include, but are not limited to, saline, buffered saline (such as phosphate buffered saline), dextrose, liposomes, water, glycerol, ethanol and combinations thereof.

Subcutaneous administration of the subcutaneous dosage forms described herein may be undertaken in any effective, convenient manner effective for treating a patient's disease. The dosage form may be a liquid form or a solid form. Liquid forms may be ready for use or prepared as concentrates which are then diluted prior to subcutaneous administration. Solid forms may suitably be reconstituted in an appropriate administration vehicle for sub-cutaneous administration. In therapy or as a prophylactic, the active agent administered to an individual as an injectable composition may be, for example, a sterile aqueous dispersion, preferably isotonic.

According to a further aspect of the invention, there is provided a liquid dosage form of a modified blood coagulation factor for subcutaneous administration no more than once a month wherein the dosage form has a $C_{max}$ of at least 10% and no more than 90% of that achieved by intravenous administration of the modified blood factor for use in the treatment of a blood clotting disorder.

This aspect of the invention also includes methods of treatment of a blood clotting disease or trauma in a subject comprising administering subcutaneously a dosage form of a modified blood clotting factor as defined herein to a subject in need thereof.

The invention therefore also provides the use of a modified blood clotting factor in the manufacture of a medicament comprising a dosage form as defined herein for the treatment of a blood clotting disorder in a subject wherein said medicament is for sub-cutaneous administration and has a $C_{max}$ of at least 10% and no more than 90% of that achieved by intravenous administration of the modified blood factor. Suitably, the $C_{max}$ is from 20% to 80%, or from 30% to 70%, or from 40% to 60%. In one embodiment, $C_{max}$ is 75 to 80% and the blood factor may be FVII. In another embodiment $C_{max}$ is 10% to 25% and the blood factor may be FVIII. In yet another embodiment $C_{max}$ is 40% to 60% and the blood factor may be FIX.

Blood clotting diseases or disorders may be characterised by a loss of function of a blood clotting factor, or the generation of auto-antibodies. Examples of blood clotting diseases include haemophilia A and haemophilia B.

Factor VIIa can be used in the treatment of bleeding episodes in haemophilia A or B, or in treatment of patients who have developed inhibitory antibodies against FVIII or IX, respectively. Factor VIII can be used in the treatment of bleeding episodes in patients with haemophilia A and Factor IX can be used in the treatment of patients with haemophilia B.

As used herein, the term "treatment" includes any regime that can benefit a human or a non-human mammal. The treatment of "non-human mammals" extends to the treatment of domestic mammals, including horses and companion animals (e.g. cats and dogs) and farm/agricultural animals including members of the ovine, caprine, porcine, bovine and equine families. The treatment may be in respect of any existing condition or disorder, or may be prophylactic (preventive treatment). The treatment may be of an inherited or an acquired disease. The treatment may be of an acute or chronic condition.

The subcutaneous dosage forms of the invention may be employed alone or in conjunction with other compounds, such as therapeutic compounds or molecules, e.g. anti-inflammatory drugs, analgesics or antibiotics, or other pharmaceutically active agents which may promote or enhance the activity of Factor VII, Factor VIII, Factor IX, Factor X, Factor Xa, Factor XI, Factor VIIa, Factor V, Factor XIII, von Willebrand's Factor or Protein C, for example another blood coagulation factor. Such administration with other compounds may be simultaneous, separate or sequential. The components may be prepared in the form of a kit which may comprise instructions as appropriate.

Levels of activity in the blood coagulation cascade may be measured by any suitable assay, for example the Whole Blood Clotting Time (WBCT) test or the Activated Partial Thromboplastin Time (APTT).

The Whole Blood Clotting Time (WBCT) test measures the time taken for whole blood to form a clot in an external environment, usually a glass tube or dish.

The Activated Partial Thromboplastin Time (APTT) test measures a parameter of part of the blood clotting pathway. It is abnormally elevated in Haemophilia and by intravenous heparin therapy. The APTT requires a few milliliters of blood from a vein. The APTT time is a measure of one part of the clotting system known as the "intrinsic pathway". The APTT value is the time in seconds for a specific clotting process to occur in the laboratory test. This result is always compared to a "control" sample of normal blood. If the test sample takes longer than the control sample, it indicates decreased clotting function in the intrinsic pathway. General medical therapy usually aims for a range of APTT of the order of 45 to 70 seconds, but the value may also be expressed as a ratio of test to normal, for example 1.5 times normal. A high APTT in the absence of heparin treatment can be due to Haemophilia, which may require further testing.

The invention also provides a kit of parts comprising a subcutaneous dosage form of invention, and an administration vehicle including injectable solutions for sub-cutaneous administration, said kit suitably comprising instructions for use thereof.

In one embodiment of the invention, there is provided a dosage form of a pharmaceutical composition of a modified blood coagulation factor (suitably, Factor VII, Factor VIII, Factor IX, Factor X, Factor Xa, Factor XI, Factor VIIa, Factor V, Factor XIII, von Willebrand's Factor or Protein C) for subcutaneous administration which when formulated for subcutaneous administration to a subject provides an no more than once per month dosage form sufficient to maintain a whole blood clotting time in said subject of less than 15 minutes. The dosage formulation may suitably have a $C_{max}$ of at least 10% and no more than 90% compared to an equivalent reference dosage form when administered intravenously.

The invention therefore provides a dosage form of a pharmaceutical composition of a modified blood coagulation factor selected from the group consisting of Factor VII, Factor VIII, Factor IX, Factor X, Factor Xa, Factor XI, Factor VIIa, Factor V, Factor XIII, von Willebrand's Factor or Protein C for subcutaneous administration which when formulated for subcutaneous administration to a subject provides an no more than once per month dosage form sufficient to maintain a whole blood clotting time in said subject of less than 12 minutes.

In one embodiment the invention therefore provides a dosage form of a pharmaceutical composition of 25 to 50 IU/kg of a PEGylated blood coagulation factor selected from the group consisting of Factor VIIa, Factor VIII and Factor IX for subcutaneous administration no more than once per week.

A liquid dosage form of the invention may comprises a modified blood coagulation factor as defined herein for subcutaneous administration no more than once per month wherein the dosage form has a $C_{max}$ of at least 10% and no more than 90% for use in the treatment of a blood clotting disorder.

Such compositions may find particular utility in methods of treatment of a blood clotting disease or trauma in a subject comprising administering subcutaneously a dosage form of a blood clotting factor according to the invention to a subject in need thereof.

The dosage forms of the invention when administered subcutaneously have a bioavailability and efficacy comparable to the levels the respective modified analogue blood clotting factor when administered intravenously by both circulating titre and clotting activity.

In another embodiment of the invention, there is provided a dosage form for sub-cutaneous administration comprising a blood clotting factor as defined herein modified to a straight-chain, mono-disperse polyethyleneglycol molecule via a three carbon bridge moiety to a single disulphide bond in the protein.

A liquid dosage form of the invention may be prepared by formulating the PEG-conjugated blood clotting factor in an aqueous solution, buffered to physiological and in the presence of a non-ionic surfactant and optionally a stabiliser.

Preferred features for the second and subsequent aspects of the invention are as for the first aspect mutatis mutandis.

The product impact of a modified agent in accordance with the invention has been shown to be superior to the same modified agent delivered intravenously. Product impact can be defined as being the improvement in, for example, the WBCT. This defined as initial WBCT divided by the WBCT at a particular time point. Using this method, modified blood clotting agents delivered subcutaneously consistently showed a higher product impact than the same product delivered intravenously at the same time point.

According to the present invention, there is a lower immune response arising from subcutaneous administration of therapeutic agents which have been modified, for example by the addition of a biocompatible polymer. This effect is diametrically opposite to what would be expected prior to the present invention by someone of ordinary skill in the art of administration of pharmaceutical formulations. For example, in the field of blood factor formulations, it is generally accepted that administration of an unmodified blood factor subcutaneously would be expected to stimulate an immunogenic response (creation of FVIII inhibitors) or to trigger an immune response by the existing population of FVIII inhibitors.

Relative immune response to blood clotting factors can be measured in Bethesda units. A Bethesda unit (BU) is a measure of blood coagulation inhibitor activity. According to Practical Haemostasis, "1 Bethesda Unit (Bu) is defined as the amount of inhibitor in a plasma sample which will neutralise 50% of 1 unit of Factor VIII:C in normal plasma after 2 hr incubation at 37° C." (Schumacher, Harold Robert (2000). *Handbook of Hematologic Pathology*. Informa Health Care, p. 583).

In the present invention, a very surprising outcome has been found. In order to lower the incidence of immune (inhibitor) responses it is proposed to adopt subcutaneous administration where the level of immune response is directly related to the level of systemic exposure. By providing a subcutaneous delivery, the $C_{max}$ can be radically lowered and in so doing there is a lowering of immune response.

As an example, the present invention describes the surprising depot effect encountered with blood factors when conjugated to polymers such as PEG. Moreover, the results show that it is possible to engineer the rate at which blood factors are made available from the sub-cutaneous space by manipulating the level of hydration imposed on the protein from the size (or amount) of PEG.

From the results shown in the present application it can be seen that for therapeutic agents modified by one polymer chain that such agents have a slower rate of entry into the plasma than the corresponding di-conjugated forms where two polymer chains are added.

In other words, the mono-conjugated products would appear to have more of the protein exposed by comparison to the di-conjugated products. This condition would mean that the higher-order conjugated forms would be more water dispersible and therefore a fast rate of entry via the lymphatic vessels into the plasma.

Surprisingly therefore, to achieve the longest duration of depot release, a lesser degree of modification is required. Without being bound by theory, this can be rationalised by the lesser degree of modification exposing some of the therapeutic agent to the sub-cutaneous tissue which confers a slow rate on the diffusion through the lymph. By contrast the higher degree of modification covers the therapeutic agent completely leaving the product free to quickly enter the blood circulation.

Overall, there is a very surprising total effect whereby the combination of modification followed by subcutaneous delivery, renders an observed 35-fold increase in apparent half-life following subcutaneous (SQ) administration).

Finally, it can be seen overall that the bioavailability favours the higher order conjugated forms, confirming that the higher the level of modification and hydration levels promote a higher degree of mobility and therefore bioavailability.

All features of each aspect apply to all other aspects of the invention, mutatis mutandis.

BRIEF DESCRIPTION OF DRAWINGS

Reference is also made herein to the following drawings in which.

DETAILED DESCRIPTION

Figure 1:
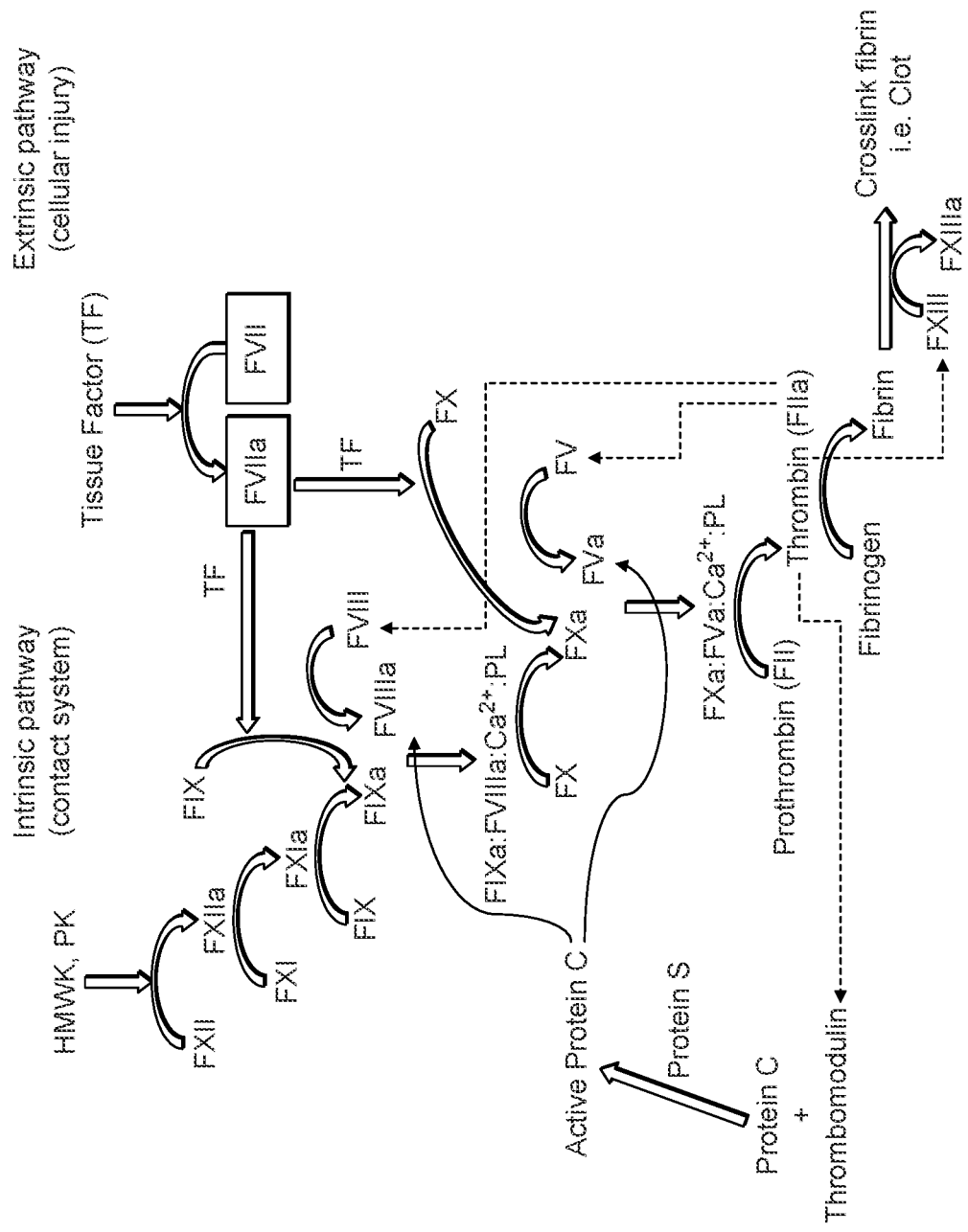
FIG. 1 shows the blood coagulation cascade. Abbreviations: HMWK—High Molecular Weight Kininogen; PK—Prekallikrein; PL—Phospholipid.
Figure 2:
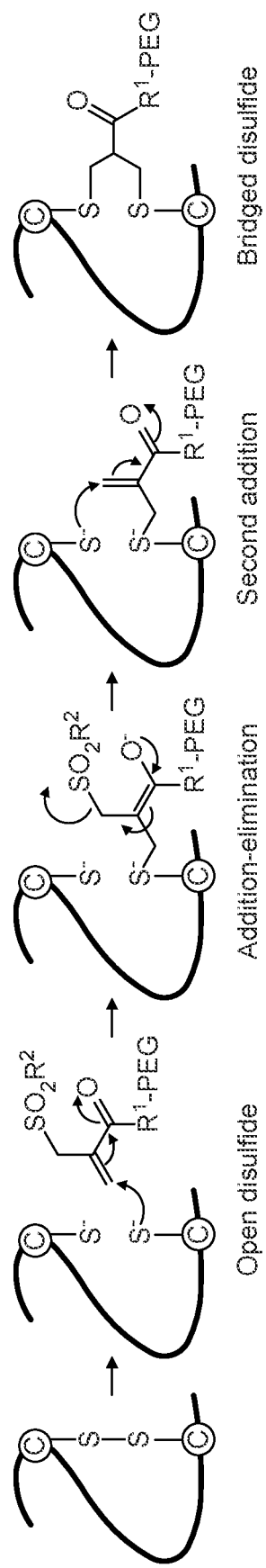
FIG. 2 shows the steps involved in disulphide-specific biopolymer conjugation chemistry with the use of a PEGylation reagent as an example of a conjugation reagent (from Shaunak et al. in Nat. Chem. Biol. 2006; 2(6):312-313).

The invention will now be further described by way of reference to the following Examples which are included for the purposes of illustration only and should not be construed as being limiting. References to subcutaneous administration of dosage formulations of the invention are given as SQ (s.c.) and intravenous administration as IV (i.v.).

Example 1: Preparation of Dosage Forms and Administration Subcutaneously

The study includes an assessment of the bioavailability and efficacy of hrFIX following subcutaneous administration. Naked (unPEGylated) hrFIX was compared to its PEGylated analogue by both circulating titre and clotting activity.

10 kDa PEGylated hrFIX was prepared following standard technology whereby 10 kDa, straight-chain, monodisperse polyethyleneglycol was conjugated via a three carbon bridge to a single disulphide bond.

The test article was prepared for administration by forming a suitable aqueous solution, buffered to pH 6.8 with 10 mM histidine, 40 mM NaCl and 0.005% Tween® 80. 1 mM benzamidine was added as a stabiliser.

On the basis that dilution studies of hrFIX showed comparable clotting times with PEGrFIX at 25% dilution, the allocated potency for this study was 4× protein equivalents. The control article was supplied as a lyophilised powder and prepared for administration following the enclosed instructions for reconstitution. The delivery vehicle is identical to that described above for PEG.

As an adjunct to this study it was decided to explore the possibility of subcutaneous (SQ) administration of rFIX. The prospect of the PEGylated form of rFIX being suitable for SQ administration emerged from the above observation that PEG provided a shielding effect of the protein. Historically the SQ route was considered unavailable for FIX since there was the concern that this would exacerbate the incidence of antibody production and would not translate into meaningful quantities in the blood.

In this part of the study PEGhrFIX 50 IU/Kg was administered subcutaneously to an additional test animal (Dog 1) and compared to 2 SQ administrations of naked hrFIX) to 2 other test subjects, namely Dog 6 and Dog 2 respectively.

In this particular representation, each animal had a slightly different baseline so for ease of comparison, the pre-administration APTT level was normalised to 1. Dog 1 and Dog 2 were the test subjects in the previous PEGrFIX trial in January 2010 from which the recorded plasma titres following intravenous administration were available for comparison.

Blood samples were taken over a regular time course to follow the decay of titre and the effect on blood coagulation. Table 1 is a summary of the titres measured at 22 hours as circulating FIX following intravenous administration.

TABLE 1

| Subject | Article | Dose (IU/Kg) | Titre |
| --- | --- | --- | --- |
| Dog 1 | PEGhrFIX | 50 | 9.9 |
| Dog 2 | Benefix ® | 50 | 5.6 |
| Dog 3 | hrFIX | 50 | 5.1 |
| Dog 4 | PEGhrFIX | 50 | 9.7 |
| Dog 5 | PEGhrFIX | 100 | 11.1 |
| Dog 6 | PEGhrFIX | 100 | 10.2 |
| Dog 7 | PEGhrFIX | 150 | 17.6 |
| Dog 8 | PEGhrFIX | 150 | 75.5 |

Table 2 shows comparison of measured Circulating FIX Titre at 22 Hours Following subcutaneous (SQ) Administration.

TABLE 2

| Subject | Article | Dose (IU/Kg) | Titre |
| --- | --- | --- | --- |
| Dog 1 | PEGhrFIX | 50 | 7.8 |
| Dog 6 | hrFIX | 50 | 1.7 |
| Dog 2 | Benefix ® | 25 | ND |

It can be seen that 25 IU/Kg of Benefix® by the SQ route was undetectable in circulation and 50 IU/Kg of PEGhrFIX was barely detectable in plasma. In stark contrast the SQ administration of PEGhrFIX was at a level (7.8) approaching that of the IV administered product (9.9).

Figure 3:
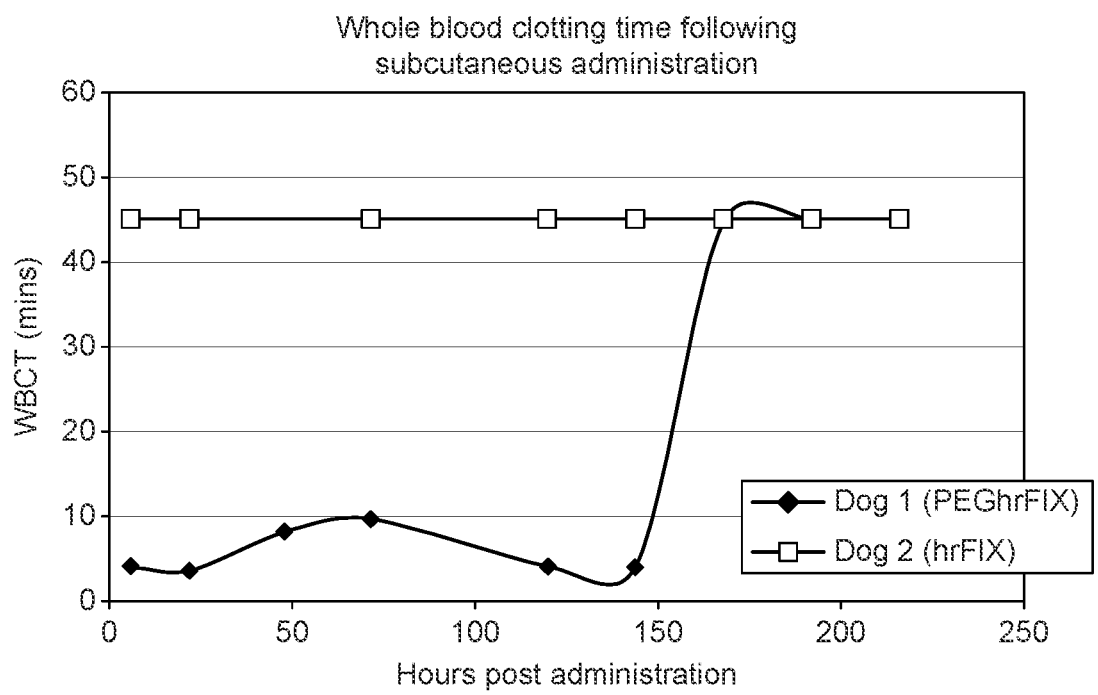
FIG. 3 shows Whole Blood Clotting Times (WBCT) following subcutaneous (SQ) administration of PEGhrFIX to subject Dog 1 and hrFIX to subject Dog 2.
Figure 4:
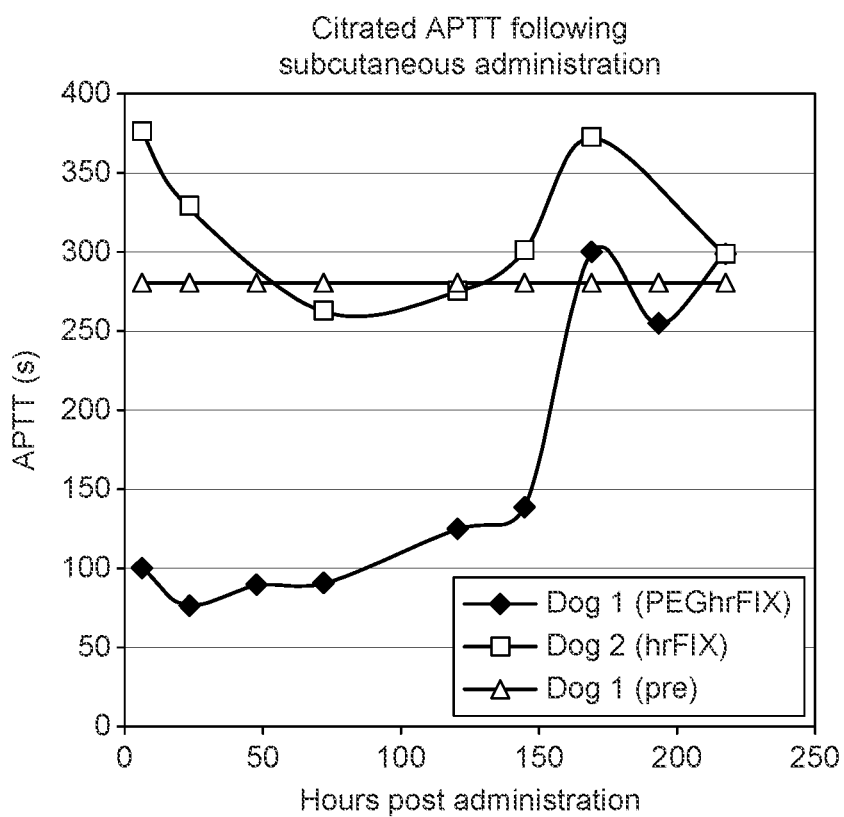
FIG. 4 shows APTT (Activated Partial Thromboplastin Time) Values with Time Following SQ Administration.
Figure 5:
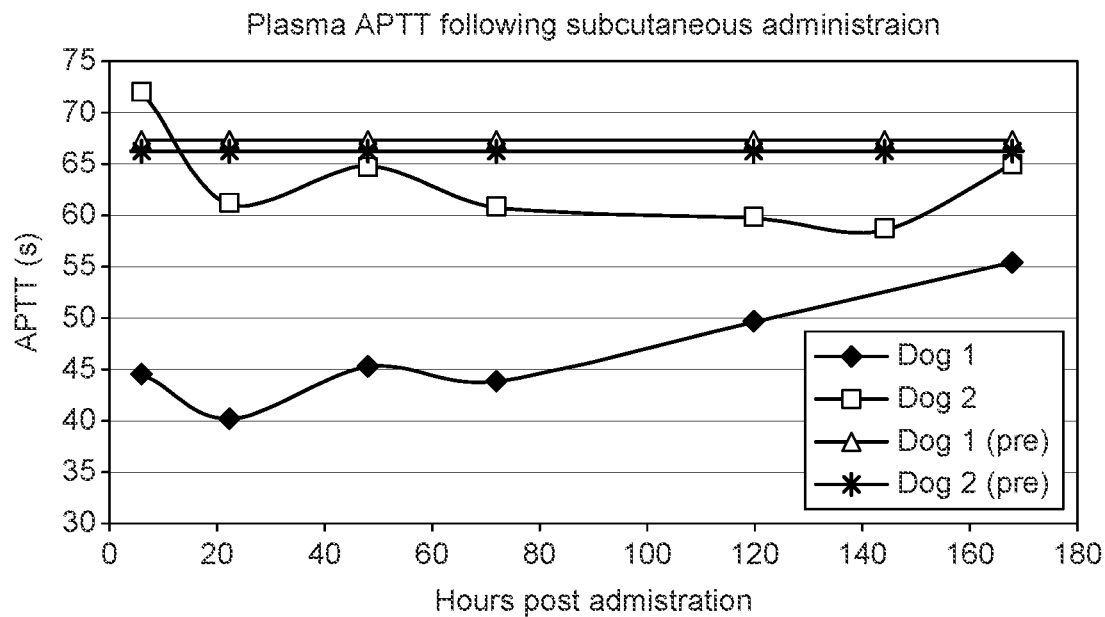
FIG. 5 shows APTT of Retained Plasma Following SQ Administration.

The effect of these titres on the correction of clotting times was then investigated. In the first instance the whole blood clotting times were recorded. The WBCT following subcutaneous administration is displayed in Table 3 and in FIG. 3. In addition, APTT on Hemochron® Junior was also recorded and the values are shown in Table 4 below (Whole blood citrated) and in FIG. 4 after subcutaneous administration. The APTT values on retained plasma samples are displayed in Table 5 and in FIG. 5 also following subcutaneous administration.

TABLE 3

Whole Blood Clotting Time (minutes)**
Following Subcutaneous Administration

| Hours | Dog 1 (PEGhrFIX) | Dog 2 (hrFIX) |
|---|---|---|
| 6 | 4 | 45* |
| 22 | 3.5 | 45 |
| 48 | 8 | 45 |
| 72 | 9.5 | 45 |
| 120 | 4 | 45 |
| 144 | 4 | 45 |
| 168 | 45 | 45 |
| 192 | 45 | 45 |
| 216 | 45 | 45 |

*Note
45 minutes was the time at which monitoring was ceased, due to no clot having been formed, according to standard procedures.
**both dogs were naïve dogs, meaning they had not previously been exposed to FIX.

TABLE 4

Citrated APTT Following Subcutaneous Administration

| | Dog 1 (PEGhrFIX | Dog 2 (hrFIX) |
|---|---|---|
| Pre | 279.7 | 225.1 |
| 6 | 99.4 | 375.5 |
| 22 | 75.6 | 328.7 |
| 48 | 88.6 | |
| 72 | 90.1 | 261.7 |
| 120 | 124.4 | 274.5 |
| 144 | 138.9 | 301 |
| 168 | 300 | 372.5 |
| 192 | 254.2 | |
| 216 | 300 | 298.3 |

TABLE 5

APTT Following Subcutaneous Administration

| | Dog 1 (PEGhrFIX | Dog 2 (hrFIX) |
|---|---|---|
| Pre | 67.2 | 66.3 |
| 6 | 44.6 | 71.9 |
| 22 | 40.2 | 61.1 |
| 48 | 45.3 | 64.7 |
| 72 | 43.9 | 60.7 |
| 120 | 49.6 | 59.6 |
| 144 | — | 58.5 |
| 168 | 55.4 | 64.9 |

Figure 6:
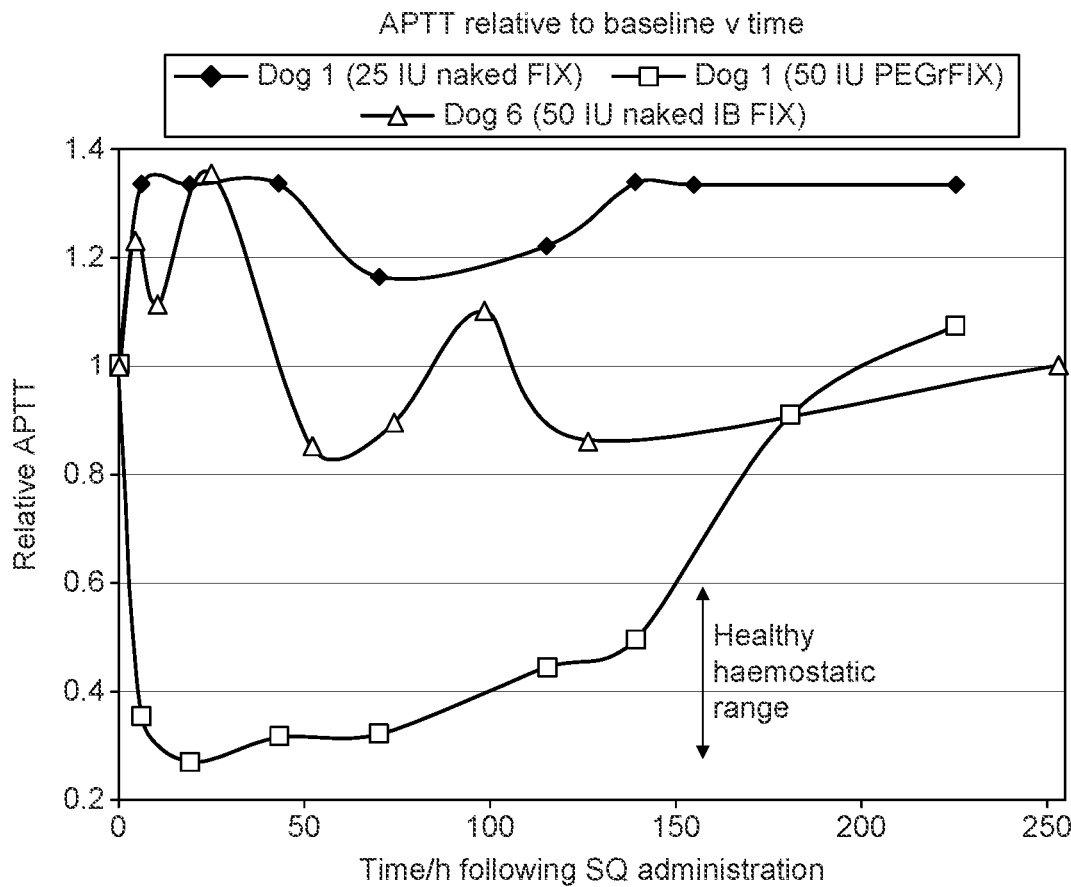
FIG. 6 shows APTT Relative Values to Baseline Following SQ Administration.

FIG. 6—This collection of data clearly shows that naked rFIX is (practically) not bioavailable from subcutaneous injection. This is entirely expected from published literature and general knowledge of the art. It is all the more surprising then such high circulating titres of rFIX can be detected following subcutaneous injection of PEGhrFIX. Indeed it can be seen in table 10 that ca 80% of the subcutaneously injected PEGrFIX is available for participation in haemostatic control.

The contrast is starkest in the measured clotting times, both WBCT and APTT for rFIX are barely corrected, whereas PEGhrFIX from subcutaneous injection corrects clotting times immediately. The duration of haemostasis by these measurements is prolonged to approximately 1 week from a single 50 IU/Kg subcutaneous injection.

Example 2: Dog 9 Subcutaneous Administration (SQ) of hrFIX

Given the success of the above SQ studies it was decided to conduct a further single SQ administration of PEGhrFIX and similarly follow haemostatic control over an extended period. The test subject chosen was a naïve subject Dog 9 to explore the influence of neutralising antibodies on the SQ route of administration.

Studies of human blood factors in dogs are confounded by the response of the canine immune system to a human protein. Human rFIX is a xenoprotein therefore in canine studies and neutralising antibodies should be expected at some point following administration of the test article. Indeed when test subjects are reintroduced to human blood factors the production of antibodies is more pronounced and speedier. The subjects Dog 1 and Dog 7 following subcutaneous administration have a shortened haemostasis period as a consequence.

The test subject Dog 9 was a naïve animal and was given a small subcutaneous dose and therefore revealed the true sustained protection that PEGylated blood factors of this invention can provide. Since Dog 9 had no previous exposure to human blood factors the true underlying (and highly surprising) result was observed.

Figure 7:
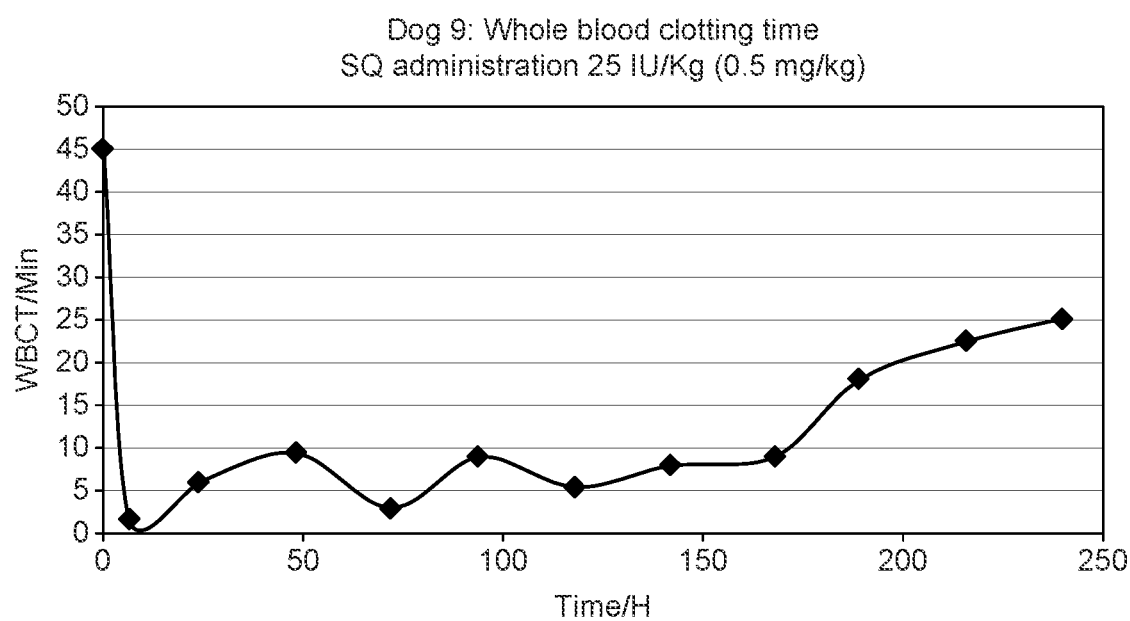
FIG. 7 shows subject Dog 9 WBCT following 25 IU/Kg SQ Administration.

FIG. 7 shows results for WBCT following 25 IU/Kg subcutaneous (SQ) administration of PEGylated IB1001 to Dog 9 of a dose of 1 ml (volume 1 ml)) and also in Table 6 below.

TABLE 6

| Time (hours) | WBCT (minutes) | FIX Titre (% Normal) | APTT (seconds) |
|---|---|---|---|
| Pre | 45 | | 67.2 |
| 6 | 1.75 | 0.68 | 53.8 |
| 24 | 6 | 2.46 | 50.9 |
| 48 | 9.5 | 2.42 | 49.8 |
| 72 | 3 | 1.69 | 55.6 |
| 94 | 9 | 1.24 | 57.7 |
| 118 | 5.5 | 1.13 | 53.2 |
| 142 | 8 | 0.66 | 56.3 |
| 168 | 9 | 0.28 | 61.4 |
| 189 | 18 | ND | 64.3 |
| 216 | 22.5 | ND | 47.7 |
| 240 | 25 | ND | 59.7 |
| 336 | | | 61.4 |

Example 3: Comparative Example

Comparison of intravenous and subcutaneous administration of FIX and PEG-FIX.

TABLE 7*

| Animal | Dose IU/kg | Type | IV $C_{max}$ ng/ml | SQ $C_{max}$ ng/ml | SQ/IV % Cmax |
|---|---|---|---|---|---|
| Beagle | 200 | BFIX | 4517.5 | 550.7 | 12% |
| Haemophilia B (HB) dog | 200 | BFIX | 7916 | 658.3 | 8.2% |

*from McCarthy et al Thromb. Haemost. 87(5) 824-830, (2002).

TABLE 8

| Animal | Dose IU/kg | Type | IV % Normal | SQ % Normal | SQ/IV % Cmax |
|---|---|---|---|---|---|
| Dog 1 | 50 | PEGFIX | 9.9 | 7.8 | 78.8% |
| Dog 7 | 50 | PEGFIX |  | 7.8 |  |
| Dog 6 | 50 | hrFIX |  | 1.7 |  |
| Dog 2 | 25 | BFIX |  | ND |  |

BFIX = Benefix ®
PEGFIX = PEG-hrFIX

Results show a $C_{max}$ of the subcutaneous dose of 78.8% of the intravenous dose. The percentage values for IV and SQ compared to normal appear to be low but are actually experimental artefacts. It is assumed that the FIX in each case is being spun down with the cells as the samples are prepared. It can be seen that the value of 9.9% for an intravenous dose is actually a representation of a good result. Consequently, the comparison with 7.8% for a subcutaneous dose is favourable as indicated by the calculated $C_{max}$ value given.

Conclusions:

Administration of hrFIX by subcutaneous injection of both 25 and 50 IU/Kg resulted in a barely detectable circulating titre and did not correct haemophilia in the canine subjects.

In stark contrast to the above, subcutaneous dosing of 50 IU/Kg of PEGhrFIX gave rise to approximately 80% bioavailability and corrected clotting times to be within the normal range for duration of 1 week.

Example 4: Factor VIIa with 20 kDa PEG

This example reports a study on PEGFVIIa Bioavailability of Blood Factor from Subcutaneous Injection. Two haemophilic dogs (HB) were treated with equipotent quantities of PEGFVIIa at time 0; one intravenously (IV), one subcutaneously (SQ). Blood samples were taken and the plasma recovered to be measured for FVIIa protein. The table of results display a bioavailability from subcutaneous administration of 89.5%.

TABLE 9

| Time | PEGylated blood factor VIIa plasma titres | |
|---|---|---|
| (hours) | IV | SQ |
| 0 | 9.5 | 9.5 |
| 4 | 167.5 | 73.9 (max) |
| 12 | 122.2 | 62.4 |
| 24 | 45.7 | 57.5 |
| 48 | 23.1 | 39.6 |
| 72 | 9.3 | 22.5 |
| Average | 62.88 | 44.23 |
| Max/Average | 2.66 | 1.67 |

The presence of PEG confers aqueous solubility which facilitates mobility in lymph vessels. The data shows a steady controlled infusion of FVIIa rather than the bolus peak and trough associated with the IV injection.

The area under the curve indicates 89.5% bioavailability for PEGylated FVIIa and a more steady state of the level of FVIIa when delivered subcutaneously.

Example 5: PEGFVIII Drug Products

To make the comparison, reference is made to Kogenate® FS (a commercially available recombinant FVIII). The PEGylated excipient, Tween® 80 is used in large quantity. Polysorbate, Tween® 80, has a molecular weight of 1310 g/mol, 880 g of which is derived from PEGylation (total monomer units of 20 which each carry 44 g/mol, (CH2-CH2-O)).

The calculation is thus:
Molar PEG Length Equivalent:
Reference: Product Monograph Example taken 250 IU Vial

| | |
|---|---|
| FVIII Molecular weight | 3.00E+05 g/mol |
| IU/g | 4.00+06 IU/g |
| IU/Vial | 2.50E+02 IU/Vial |
| Vial volumes | 2.50E+00 ml/vial |
| Polysorbate concentration | 6.40E−05 g/ml |
| Molecular weight Polysorbate | 1.31E+03 g/mol |
| Molecular weight PEG per mol Polysorbate | 880 g/mol |

TABLE 10

| FVIII Kogenate ® | Polysorbate |
|---|---|
| 4.00E+06 IU/g | 1.31E+03 g/mol |
| 3.00E+05 g/mol | 6.40E−05 g/ml |
| 1.2E+12 IU/Mol | 2.50E+00 ml/vial |
|  | 1.60E−04 g/vial |
| 2.50E+0.2 IU/Vial |  |
| 2.08E−10 Mol/vial | 1.22E−07 mol/vial |

Ratio of Tween ®/FVIII 5.86E+02
PEG equivalent Mol Wt. 5.16E+05

Therefore, in Kogenate® FS, each FVIII molecule has the equivalent of an associated 516 kDa PEG. By comparison, the PEGFVIII dosage formulation prepared according to the present invention has a single 20 kDa PEG.

Conclusions:

On a dose-for-dose basis there is a 25.8 fold reduction in polyethylene glycol; given the PEG-FVIII dosage formulation of the present invention may be administered once per week versus a prophylactic use of Kogenate® on a three times a week basis, there is a potential overall reduction of ca 80-fold reduction in the administration of PEG; and the amount of PEG administered by the FVIII dosage formulation of the present invention over a dosing period is 1.25% of that administered by Kogenate®.

Example 6: Subcutaneous Administration FVIIa

The objectives of this study were to investigate the pharmacokinetics of TheraPEGylated and non-TheraPEGylated recombinant human FVIIa (TheraPEGrFVIIa and FVIIa respectively) following intravenous and subcutaneous administration in haemophilic B dogs.

TheraPEGylation of transgenic FVIIa (rFVIIa) was carried out according to WO 2011/135308. TheraPEGrFVIIa was supplied to the test site as a lyophile in multiple batches which, on reconstitution with high purity water, resulted in 1 mg/ml TheraPEGrFVIIa in a physiologically acceptable buffer which maintained activity of FVIIa The experimental animals were Lhasa Apso-Basenji cross dogs with congenital severe haemophilia B caused by a 5-bp deletion and a C→T transition in the F9 gene that results in an early stop codon and unstable FIX transcript. Prior to dosing, all dogs were tested to verify normal health status, including complete blood chemistry, serum chemistry profile fibrinogen, fibrinogen derived peptides (FDPs), thrombin time and urinary analysis. Drugs given intravenously (IV) were given as a bolus injection into the cephalic vein. Subcutaneous (SQ) doses were given between the scapula as a single dose.

Individual batches of TheraPEGrFVIIa were reconstituted and then combined in order to produce a single dose solution used to dose the animals as described in Table 11.

TABLE 11

| Dog Subject and Code (Gender) | Dog Weight (kg) | Drug | Dose route | Dose Level (ug/kg) | Dose Amount (mg) |
|---|---|---|---|---|---|
| Dog 9 HB1 (Male) | 5.4 | TheraPEG-rFVIIa | SQ | 800 | 4.32 |
| Dog 3 HB2 (Male) | 11.4 | rFVIIa | SQ | 200 | 2.28 |
| Dog 5 HB3 (female) | 5.6 | TheraPEG-rFVIIa | IV | 800 | 4.48 |
| Dog 7 HB4 (female) | 10.0 | rFVIIa | IV | 200 | 2.0 |
| Dog 10 HB5 (female) | 5.5 | TheraPEG-rFVIIa | IV | 1600 | 8.8 |
| Dog 11 HB6 (male) | 4.8 | TheraPEG-rFVIIa | SQ | 1600 | 7.68 |

A 5 ml blood sample was protocolled to be taken from each dog at the following times points:

Pre-drug administration and at 10, 30 minutes, 1, 2, 4, 8, 12, 18, 24, 36, 48, 72, 96, 120, 144, 168, 192, 216 and 240 hours post-dose.

4 ml of the blood sample was transferred into a tube containing 0.109M tri-sodium citrate anticoagulant (9:1 v/v) on ice. Plasma was prepared by centrifugation of the remaining citrated blood and the resulting plasma samples were stored in aliquots at −80° C. An aliquot of plasma was assayed for FVIIa concentration by ELISA.

The Stago Asserachrom VII:Ag ELISA assay is an enzyme linked immunoassay procedure for the quantitative determination of Factor VII/VIIa concentration in plasma samples. The assay is a sandwich ELISA which comprises of microtitre wells pre-coated with a rabbit anti-human FVII antibody. Because the antibody has a different affinity for FVIIa than for PEG-FVIIa, a standard curve was prepared by dilution of a protein appropriate to the FVIIa that is present in the test plasma, i.e. rFVIIa (0.78 to 50 ng/ml) for assay of plasma from dogs that were administered rFVIIa, or PEG-rFVIIa (0.78 to 50 ng/ml) for assay of plasma from dogs that were administered PEG-rFVIIa.

Plasma samples were diluted to an appropriate concentration to fall within the standard curve. Diluted plasma samples and standards were loaded and incubated at room temperature before washing and subsequent development with a rabbit anti-human FVII HRP conjugate and OPD (a colorimetric HRP substrate). The plate was read at 492 nm and the concentration of the test samples (ng/ml) is read from the standard curve.

TABLE 12

| Dose Route | Tmax (h) | Cmax (ng/mL) | AUC(0-t) (ng · h/mL) | AUC(0-∞) (ng · h/mL) | Rate (/h) | Half-life (h) | Bio. (%) |
|---|---|---|---|---|---|---|---|
| IV | 0.16 | 1643 | 2467 | 2534 | 0.2994 | 2.3 | 100 |
| SQ | 7.5 | 31.3 | 276 | — | — | — | 11 |

TABLE 13

| Dose Route | Tmax (h) | Cmax (ng/mL) | AUC(0-t) (ng · h/mL) | AUC(0-∞) (ng · h/mL) | Rate (/h) | Half-life (h) | Bio. (%) |
|---|---|---|---|---|---|---|---|
| IV | 0.5 | 19372 | 128305 | 129646 | 0.0256 | 27.0 | 100 |
| SQ | 12.0 | 1378 | 84960 | 87139 | 0.0262 | 26.5 | 67 |

TABLE 14

| Dose Route | Tmax (h) | Cmax (ng/mL) | AUC(0-t) (ng · h/mL) | AUC(0-∞) (ng · h/mL) | Rate (/h) | Half-life (h) | Bio. (%) |
|---|---|---|---|---|---|---|---|
| IV | 0.5 | 26609 | 236116 | 240449 | 0.050 | 13.8 | 100 |
| SQ | 24 | 2030 | 107728 | 108454 | 0.038 | 18.3 | 45.6 |

Pharmacokinetics

Figure 8:
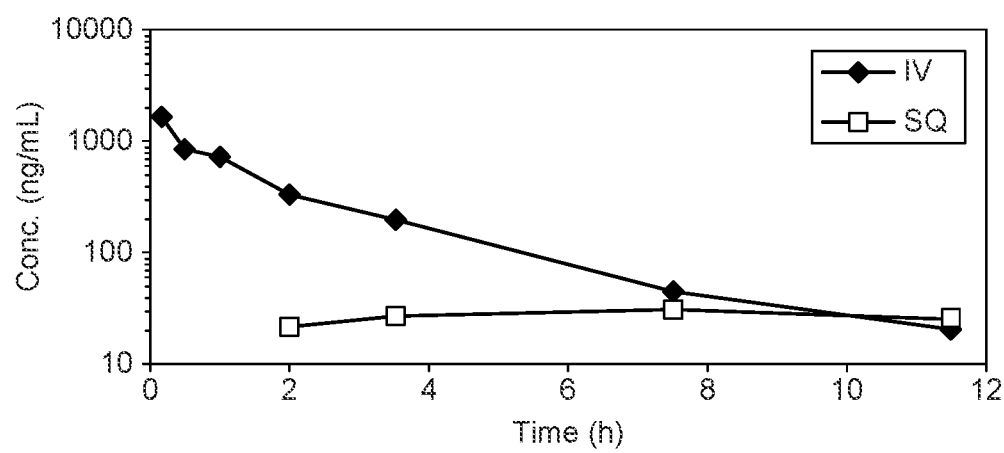
FIG. 8 shows PK profiles and parameters of FVIIa following 200 ug/kg rFVIIa.
Figure 9:
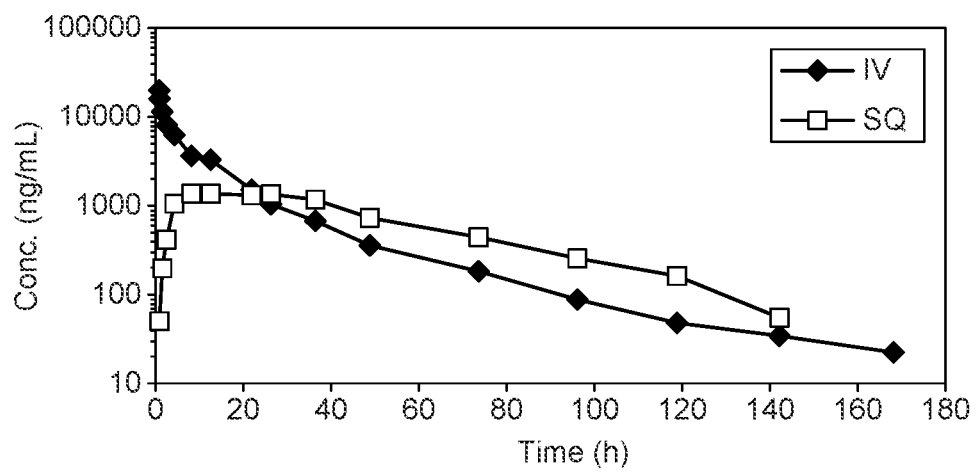
FIG. 9 shows PK profiles and parameters of FVIIa following 800 ug/kg TheraPEG-rFVIIa.
Figure 10:
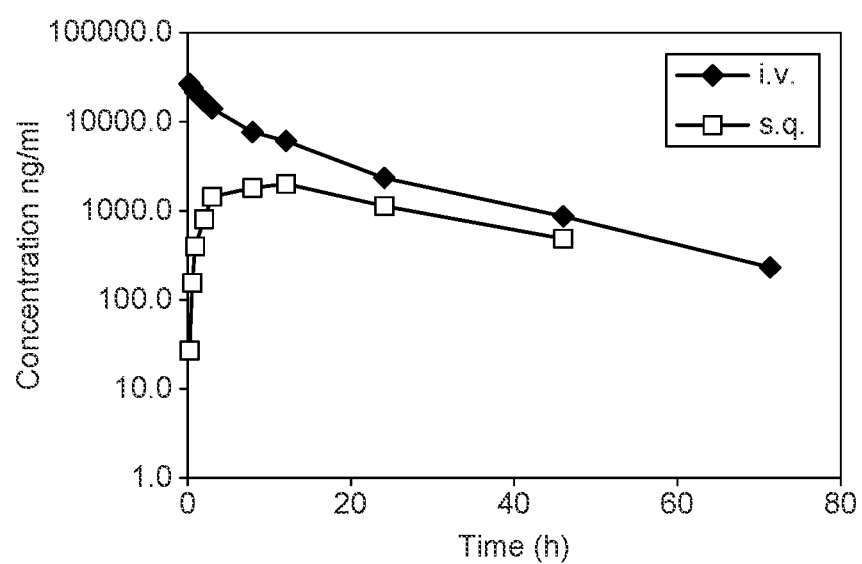
FIG. 10 shows PK profiles and parameters of FVIIa following 1600 ug/kg TheraPEG-rFVIIa.

The IV and SQ profiles and PK parameters for 200 ug/kg FVIIa, 800 ug/kg TheraPEG-rFVIIa and 1600 ug/kg TheraPEG-rFVIIa are shown in FIGS. 8, 9 and 10 (Table 12, Table 13 and Table 14). The half-life of TheraPEG-rFVIIa was found to be between 14 and 27 hours, which is a clear extension over the 2.3 hour half-life of non-PEGylated rFVIIa. The AUC of the 1600 ug/kg IV dose of TheraPEG-rFVIIa was 1.8× higher than that of the 800 ug/kg IV dose. However the 1600 ug/kg SQ dose was only 1.2× higher than that of the 800 ug/kg dose. This is reflected in the bioavailability calculations of 67% and 45% for the 800 ug/kg and 1600 ug/kg doses respectively, which represented a significant increase over the 11% SQ bioavailability observed for non-PEGylated rFVIIa.

The AUC for the 800 ug/kg IV dose of TheraPEG-rFVIIa is 84× that of the AUC following 200 ug/kg IV non-PEGylated rFVIIa and the AUC for the 800 ug/kg SQ dose of TheraPEG-rFVIIa is 300× that of 200 ug/kg SQ non-PEGylated rFVIIa.

Example 7: Subcutaneous Administration FVIII

The objectives of this study were to investigate the pharmacokinetics and pharmacodynamics of TheraPEGylated plasma derived FVIII (TheraPEG-pdFVIII) when administered intravenously and subcutaneously to haemophilic A dogs. TheraPEG-pdFVIII was prepared as described in WO 2011/135307 with a 20 kDa linear PEG and further purified to yield purified TheraPEG-pdFVIII.

The experimental animals were greyhound cross dogs which had congenital severe haemophilia A and had previously been administered canine plasma for the treatment of spontaneous bleeds, but were naïve to treatment with human FVIII. Prior to dosing, all animals were tested to verify normal health status, including complete blood chemistry, serum chemistry profile fibrinogen, fibrinogen derived peptides, thrombin time and urinary analysis.

Table 15 shows the weight of each dog and the FVIII doses that were administered. Each dog received a single dose of either TheraPEG-pdFVIII at a higher (approx. 0.14 mg/kg) or a lower (0.07 mg/kg) dose or non-PEGylated pdFVIII at 0.03 mg/kg. Intravenous (IV) administration was given as a bolus dose via the cephalic vein. Sub cutaneous (SQ) administration was given as a single dose between the scapulae.

TABLE 15

| TEST article | Dose route | Dog subject (gender) and code | Weight (kg) | FVIII Conc. (mg/ml) | Dose volume (ml) | Dose total amount FVIII (mg) | Dose (mg FVIII/kg) |
|---|---|---|---|---|---|---|---|
| TheraPEG-pdFVIII | SQ | Dog 12 (F) HA1 | 21.8 | 0.211 | 14 | 2.954 | 0.135 |
| TheraPEG-pdFVIII | SQ | Dog 13 (M) HA2 | 26.6 | 0.235 | 16 | 3.76 | 0.141 |
| TheraPEG-pdFVIII | IV | Dog 14 (F) HA3 | 20.6 | 0.211 | 14 | 2.954 | 0.143 |
| TheraPEG-pdFVIII | IV | Dog 15 (M) HA4 | 31 | 0.235 | 17.1 | 4.019 | 0.130 |
| TheraPEG-pdFVIII (low dose) | SQ | Dog 16 (M) HA6 | 28 | 0.273 | 7.0 | 1.911 | 0.068 |
| Non-PEG'd pdFVIII | SQ | Dog 17 (F) HA5 | 27.4 | 0.090* | 9.0 | 0.810 | 0.030 |

A blood sample was protocolled to be taken from each dog at the following times points. Pre-drug administration and at 10, 30 minutes, 1, 2, 4, 8, 12, 18, 24, 36, 48, 72, 96, 120, 144, 168, 192, 216 and 240 hours post-dose. Whole blood (non-citrated) was used for the whole blood clotting assay and the activated clotting time assay. The remaining blood sample was transferred into tubes containing 0.109M tri-sodium citrate anticoagulant (9:1 v/v) on ice. The activated partial thromboplastin time assay was conducted on citrated blood. Plasma was prepared by centrifugation of the citrated blood and the resulting plasma samples were stored in aliquots at −80° C. for the FVIII antigen ELISA.

Whole Blood Clotting Time Assay (WBCT)

Blood samples were divided between 2 vacutubes, (2×0.5 ml), and observed carefully with periodic and judicious levelling of the tube until a clot was determined by interruption of flow in the fully horizontal position. The quality of the clot was then observed by holding the tube in the fully inverted position. The WBCT was recorded as the mean of the total time from sample extraction until visual observation of blood clot for both samples and the quality of the clot in the inverted position was also noted.

Activated Clotting Time (ACT) and Activated Partial Thromboplastin Time (APTT)

The ACT and APTT tests were carried out using a Haemachron Jr coagulation analyzer (International Technidyne Corps.) according to the manufacturer's instructions.

The concentration of FVIII antigen in plasma samples was determined by ELISA using the Visulize FVIII antigen kit from Affinity Biologicals (Ancaster, Ontario, Canada) according to the manufacturer's instructions.

Results

Whole Blood Clotting Time (WBCT)

Haemostasis (WBCT <12 minutes) was maintained in all dogs that had received the higher dose of TheraPEG-pdFVIII (HA1-4) for between 80-100 hours. There appeared to be no difference in the WBCT profile between IV and SQ administration. A lower dose of TheraPEG-pdFVIII (HA6) given SQ maintained haemostasis for between 56-75 hours.

In contrast, although non-PEGylated FVIII administered SQ reduced the WBCT, it did not result in a sustained WBCT below 12 minutes.

Activated Clotting Time (ACT)

ACT was reduced into the normal range of less than 200 seconds in all dogs that had received the higher dose of TheraPEG-pdFVIII (HA1-4) for approximately 80 hours post-dose. There was no difference in the ACT profile between IV and SQ administration.

A lower dose of TheraPEG-pdFVIII (HA6) given SQ maintained ACT below 200 seconds for at least 36 h. In contrast, although non-PEGylated FVIII given SQ reduced the ACT, it did not result in a sustained ACT below 200 seconds.

Activated Partial Thromboplastin Time (APTT)

APTT was reduced to less than 60 seconds in all dogs that had received the higher dose of TheraPEG-pdFVIII (HA1-4) for approximately 60 hours post-dose. There was no difference in the APTT profile between IV and SQ administration.

A lower dose of TheraPEG-pdFVIII (HA6) given SQ maintained APTT at less than 60 seconds for 40 h. In contrast, although non-PEGylated FVIII given SQ reduced the APTT, the shortest APTT time was 80 seconds. The reason why the APTT for this individual remained below base-line value for the duration of the study post-dose is obscure, but may be due to dog-to-dog variation.

FVIII Plasma Concentrations and Pharmacokinetics

Figure 11:
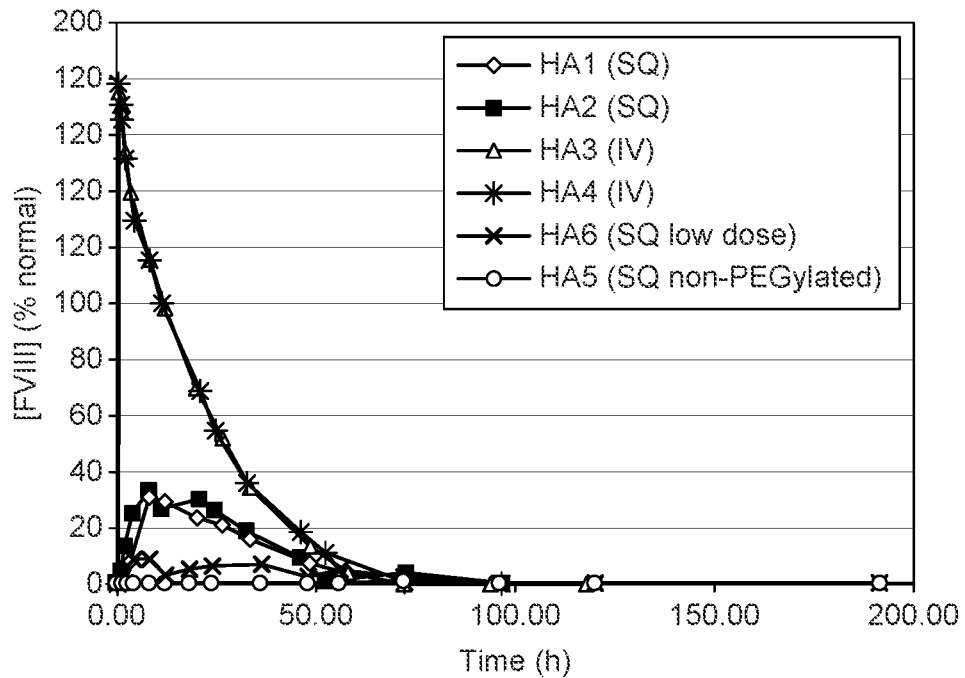
FIG. 11 shows concentration of FVIII in Plasma (all dogs).
Figure 12:
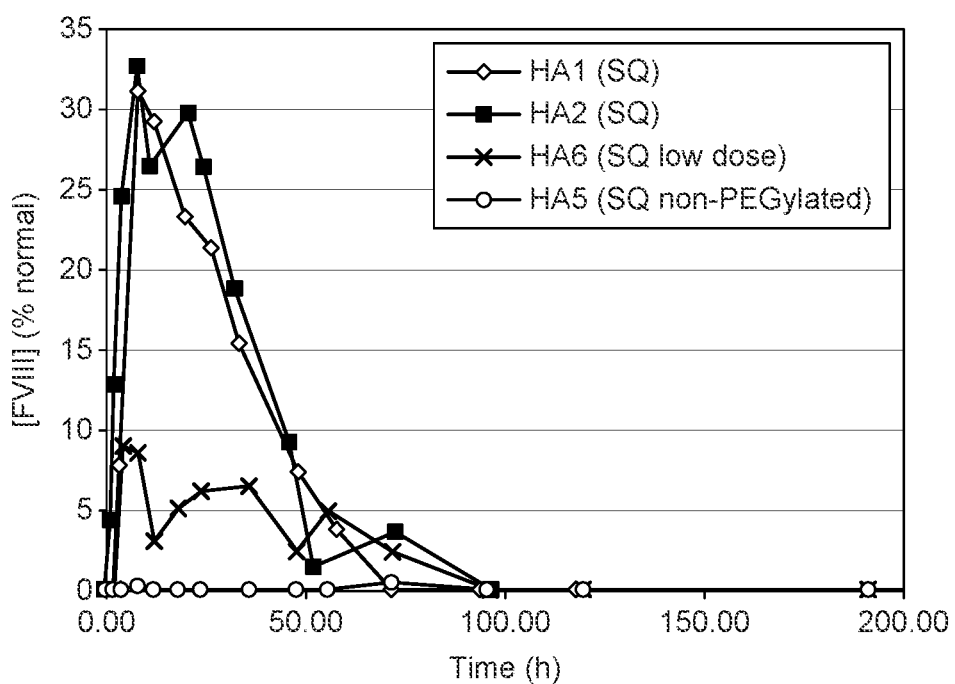
FIG. 12 shows concentration of FVIII in Plasma (SQ administered dogs only).

The FVIII plasma concentration against time in all dogs is shown in FIG. 11. The data for SQ dosed dogs alone is shown in FIG. 12. Raw data are listed in Tables 23-28. Key PK parameters are shown in Table 16.

The half-life of TheraPEG-FVIII administered SQ was 18.3h and 16.6h for HA' and 2 respectively. When administered IV, half-lives were slightly shorter at 15.2h and 13.9h for HA3 and 4 respectively. Bioavailability was calculated at 32% following SQ administration. The concentrations of FVIII following SQ administration of non-PEGylated FVIII (HA5) were mainly below the level of quantification and therefore no PK parameters could be calculated.

TABLE 16

| Dose (mg/kg) | Dog Ref. | $T_{max}$ (h) | $C_{max}$ (% Normal) | $AUC_{0-t}$ (% Normal · h) | $AUC_{0-\infty}$ (% Normal · h) | $\lambda_z$ (/h) | $t_{1/2}$ (h) |
|---|---|---|---|---|---|---|---|
| 0.135 | HA1 (SQ) | 8.00 | 31.20 | 871.4 | 1066.8 | 0.0379 | 18.3 |
| 0.141 | HA2 (SQ) | 8.00 | 32.80 | 1085.3 | 1171.7 | 0.0417 | 16.6 |
| 0.143 | HA3 (IV) | 0.16 | 176.40 | 2929.8 | 3698.0 | 0.0456 | 15.2 |
| 0.130 | HA4 (IV) | 0.16 | 179.20 | 3302.8 | 3522.8 | 0.0500 | 13.9 |
| 0.068 | HA6 (SQ) | 4.00 | 9.01 | 345.2 | 510.1* | 0.0143* | 48.4* |

*Approximate value due to variability of data.

Conclusions

Sub-cutaneous delivery of the higher dose of TheraPEG-FVIII resulted in haemostatic control for 80-100 hours following a single dose as measured by WBCT, APTT and ACT. The profile of SQ in these assays was indistinguishable from the profile of an equivalent dose of TheraPEG-FVIII given IV This clearly demonstrated the feasibility of delivering TheraPEG-FVIII SQ.

The half-life of TheraPEG-pdFVIII ranged from 13.9 to 18.3 h. This demonstrates a clear extension in half-life compared to marketed recombinant FVIII which is reported to be 7-11 h in haemophilia A dogs (Karpf et al., *Haemophilia* 17, 5 (2011)). Hence, the TheraPEG-FVIII was not only bioavailable SQ but also demonstrated an extended half-life.

The PK profile of FVIII following SQ administration of TheraPEG-pdFVIII had a much reduced $C_{max}$ and AUC compared to IV administration and bioavailability was determined to be 32%. However, at this dose level, due to the "slow release" nature of the PK curve, exposures were maintained above the 5% normal level following SQ administration for a similar amount of time as after the IV dose which is likely to explain the equivalent functional responses. The decrease in $C_{max}$ and AUC, coupled to the increase in duration of action for SQ delivered TheraPEG-FVIII highlighted potential, additional safety features of this product and dosing options.

Sub-cutaneous administration of non-PEGylated FVIII resulted in no detectable FVIII in plasma and although clotting times were reduced, there was no sustainable maintenance of haemostasis. This demonstrated that non-PEGylated FVIII had a very low SQ bioavailability, but that very small amounts of FVIII can affect haemostasis. In contrast to non-PEGylated FVIII, a low dose of TheraPEG-pdFVIII resulted in plasma levels of up to 9% normal and haemostasis was maintained for 56-75 hours. Therefore, the addition of TheraPEG to pdFVIII resulted in a greater bioavailability and functional response when administered SQ. In conclusion, this study clearly demonstrated that TheraPEGylation of FVIII resulted in a superior product that can be administered subcutaneously with an extended duration of action.

TABLE 17

HA1 (SQ PEG-pdFVIII) Dog 12

| Time (h) | WBCT (min) | APTT (min) | ACT (min) | ELISA (% normal) |
|---|---|---|---|---|
| 0.00 | 40.00 | 186.95 | 378.00 | 0 |
| 0.16 | 31.00 | 178.4 | 400 | 0 |
| 0.50 | 32.00 | 168.1 | 319 | 0 |
| 1.00 | 8.50 | 114.1 | 229 | 0 |
| 2.00 | 8.75 | 81.3 | 241 | 0 |
| 3.50 | 7.00 | 57.3 | 177 | 7.8 |
| 8.00 | 7.50 | 40.4 | 167 | 31.2 |
| 12.00 | 6.50 | 51.4 | 183 | 29.4 |
| 20.00 | 5.25 | 33.4 | 184 | 23.4 |
| 26.50 | 5.50 | 37.3 | 194 | 21.4 |
| 33.50 | 5.80 | 40.4 | 196 | 15.4 |
| 48.50 | 6.40 | 81.3 | 205 | 7.4 |
| 58.00 | 8.13 | 58.5 | 183 | 3.8 |
| 72.00 | 9.00 | 71.5 | 188 | 0.1 |
| 94.00 | 13.00 | 119.2 | 275 | 0 |
| 117.75 | 29.00 | 146.4 | 400 | 0 |
| 145.50 | 33.00 | 174.3 | 386 | |
| 170.00 | 31.75 | 137 | 360 | |
| 398.00 | 32.65 | 140.8 | 365 | |
| 696.00 | 30.00 | 133.4 | 347 | |

TABLE 18

HA2 (SQ PEG-pdFVIII) Dog 13

| Time (h) | WBCT (min) | APTT (min) | ACT (min) | ELISA (% normal) |
|---|---|---|---|---|
| 0.00 | 36.50 | 117.50 | 367.00 | 0 |
| 0.16 | 12.50 | 79.8 | 265 | 0 |
| 0.50 | 7.50 | 52.5 | 197 | 0 |
| 1.00 | 7.50 | 39.3 | 181 | 4.4 |
| 2.16 | 7.00 | 40.4 | 179 | 12.8 |
| 4.00 | 7.75 | 33.4 | 172 | 24.6 |
| 8.00 | 6.00 | 30.6 | 168 | 32.8 |
| 11.00 | 6.75 | 35.3 | 177 | 26.6 |
| 21.00 | 5.00 | 36.3 | 185 | 29.8 |
| 24.75 | 7.50 | 32.4 | 173 | 26.4 |
| 32.50 | 7.75 | 51.4 | 186 | 18.8 |
| 46.00 | 7.25 | 47.9 | 183 | 9.2 |
| 52.25 | 8.00 | 50.2 | 185 | 1.4 |
| 72.75 | 8.00 | 56.1 | 213 | 3.6 |
| 97.00 | 19.75 | 122.7 | 314 | 0 |
| 120.50 | 24.00 | 174.3 | 400 | |
| 143.50 | 26.00 | 176.3 | 371 | |
| 165.00 | 33.50 | 306.4 | 400 | |

TABLE 19

HA3 (IV PEG-pdFVIII) Dog 14

| Time (h) | WBCT (min) | APTT (min) | ACT (min) | ELISA (% normal) |
|---|---|---|---|---|
| 0.00 | 24.00 | 239.45 | | 0 |
| 0.16 | 4.00 | 38.3 | 174 | 176.4 |
| 0.50 | 4.00 | 38.3 | 158 | 169.4 |
| 1.00 | 4.50 | 32.4 | 174 | 172.2 |
| 2.00 | 5.50 | 37.3 | 180 | 154.8 |
| 3.50 | 6.50 | 31.5 | 179 | 140.6 |
| 8.00 | 4.50 | 44.6 | 160 | 116.4 |
| 12.00 | 4.90 | 29.6 | 166 | 98.6 |
| 20.00 | 5.00 | 28.7 | 176 | 70.2 |

TABLE 19-continued

HA3 (IV PEG-pdFVIII) Dog 14

| Time (h) | WBCT (min) | APTT (min) | ACT (min) | ELISA (% normal) |
|---|---|---|---|---|
| 26.50 | 6.00 | 42.5 | 171 | 52.2 |
| 33.50 | 6.75 | 37.3 | 163 | 35 |
| 48.50 | 7.63 | 43.5 | 179 | 13.6 |
| 58.00 | 7.13 | 44.6 | 184 | 4 |
| 72.00 | 6.00 | | 209 | 0 |
| 94.00 | 9.00 | | 234 | 0 |
| 117.75 | 19.00 | 112.4 | 320 | 0 |
| 145.50 | 26.25 | 176.3 | 347 | |
| 170.00 | 29.25 | 114.1 | 333 | |
| 398.00 | 40.00 | 142.6 | 362 | |
| 696.00 | 30.00 | 53.7 | 294 | |

TABLE 20

HA4 (IV PEG-pdFVIII) Dog 15

| Time (h) | WBCT (min) | APTT (min) | ACT (min) | ELISA (% normal) |
|---|---|---|---|---|
| 0.00 | 26.25 | 84.2 | 396 | 0 |
| 0.16 | 40.00 | 77 | 227 | 179.2 |
| 0.50 | 22.50 | 62.3 | 168 | 170.8 |
| 1.00 | 8.25 | 33.4 | 151 | 166.2 |
| 2.16 | 6.00 | 24.4 | 158 | 151.8 |
| 4.00 | 5.25 | 30.6 | 165 | 129.8 |
| 8.00 | 7.50 | 29.6 | 150 | 115.6 |
| 11.00 | 8.50 | 31.5 | 157 | 100.2 |
| 21.00 | 6.50 | 35.3 | 185 | 68.8 |
| 24.75 | 7.00 | 34.3 | 162 | 55 |
| 32.50 | 7.00 | 38.3 | 177 | 35.8 |
| 46.00 | 6.25 | 43.5 | 174 | 18.4 |
| 52.25 | 6.75 | 45.7 | 167 | 11 |
| 72.75 | 7.00 | 53.7 | 203 | 0 |
| 97.00 | 22.00 | 79.8 | 334 | 0 |
| 120.50 | 20.50 | 102.5 | 356 | |
| 143.50 | 23.50 | 178.4 | 306 | |
| 165.00 | 34.50 | 114.1 | 371 | |

TABLE 21

HA5 (SQ pdFVIII) Dog 17

| Time (h) | WBCT (min) | APTT (min) | ACT (min) | ELISA (% normal) |
|---|---|---|---|---|
| 0.00 | 31 | 104.2 | | 0 |
| 0.166 | 21 | 137 | 351 | 0 |
| 0.5 | 31.5 | 100.9 | 311 | 0 |
| 1 | 19.25 | 105.8 | 268 | 0 |
| 2 | 16 | 98.5 | 268 | 0 |
| 4 | 18 | 84.2 | 261 | 0 |
| 8 | 13.25 | 105.8 | 238 | 0.186 |
| 12 | 13 | 79.8 | 200 | 0 |
| 18 | 12.5 | 93.1 | 230 | 0 |
| 24 | 10.25 | 82.7 | 226 | 0 |
| 36 | 15.5 | 84.2 | 247 | 0 |
| 48 | 18.5 | 122.7 | 237 | 0 |
| 56 | 19.25 | 148.3 | 278 | 0 |
| 72 | 23 | | 364 | 0.489 |
| 96 | 25.5 | 122.7 | 347 | 0 |
| 120 | | 109.1 | 328 | 0 |
| 192 | 37.00 | 87.1 | 334 | 0 |
| 432 | 40 | 128 | 375 | 0 |

TABLE 22

HA6 (SQ PEG-pdFVIII Low Dose) Dog 16

| Time (h) | WBCT (min) | APTT (min) | ACT (min) | ELISA (% normal) |
|---|---|---|---|---|
| 0.00 | 31.75 | 81.3 | 321 | 0 |
| 0.166 | 39 | 104.2 | | 0 |
| 0.5 | 33.5 | 115.8 | 298 | 0 |
| 1 | 12.5 | 94.2 | 224 | 0 |
| 2 | 8.25 | 82.7 | 190 | 0.131 |
| 4 | 9 | 62.3 | 168 | 9.006 |
| 8 | 9 | 44.5 | 188 | 8.621 |
| 12 | 7.5 | 40.4 | 156 | 3.053 |
| 18 | 7 | 49.1 | 179 | 5.148 |
| 24 | 7.75 | 57.3 | 168 | 6.167 |
| 36 | 11.5 | 62.3 | 180 | 6.553 |
| 48 | 8.75 | 68.8 | 217 | 2.419 |
| 56 | 15 | 74.2 | 178 | 5.01 |
| 72 | 10.5 | 88.6 | 215 | 2.364 |
| 96 | 27 | 110.7 | 281 | 0 |
| 120 | | 90.1 | | 0 |
| 192 | 31.25 | 100.9 | 323 | 0 |
| 432 | 35.5 | 93.1 | 333 | 0 |

Example 8: Immune Response to Subcutaneous Administration in Dogs

In the present invention, it has been observed that there is a lower immune response arising from subcutaneous administration. This effect is diametrically opposite to what would be anticipated prior to the present invention by someone of ordinary skill in the art of blood factor administration. It is generally accepted that by administering subcutaneously the existing very high level of immune response (FVIII inhibitor frequency) would be exacerbated.

In the present invention, a very surprising outcome has been found. In order to lower the incidence of immune (inhibitor) responses it is proposed to adopt subcutaneous administration where the level of immune response is directly related to the level of systemic exposure. By providing a subcutaneous delivery, the $C_{max}$ can be radically lowered and in so doing there is a lowering of immune response.

In the examples of the invention, the PEGylated product is exposed to the most testing of immune environments, namely the dog system. It can be seen that the Bethesda values (units of inhibitor quantities) are highest and earliest when given intravenously. By contrast the subcutaneous deliveries have a very much lower systemic exposure as evidenced by the $C_{max}$ and a lower and later Bethesda response. Indeed the lowest value of all is the naked FVIII given SQ which has almost no systemic exposure and is never seen to give an inhibitor value. See FIG. 13/Table 23 for a representation of the data obtained.

TABLE 23

Summary

| Product & route | N (no. of subjects) | Cmax | Bethesda Units | | |
|---|---|---|---|---|---|
| | | | PRE | Day 7 | Day 14 | Day 30 |
| PEGFVIII IV | 2 | 177.8 | 0 | 0 | 20 | 17.5 |
| PEGFVIII SQ | 2 | 32 | 0 | 0 | 10 | 17 |
| PEGFVIII SQ (LD) | 1 | 9.0 | 0 | 0 | 0 | 6 |
| FVIII SQ | 1 | 0.5 | 0 | 0 | 0 | 0 |

Figure 13:
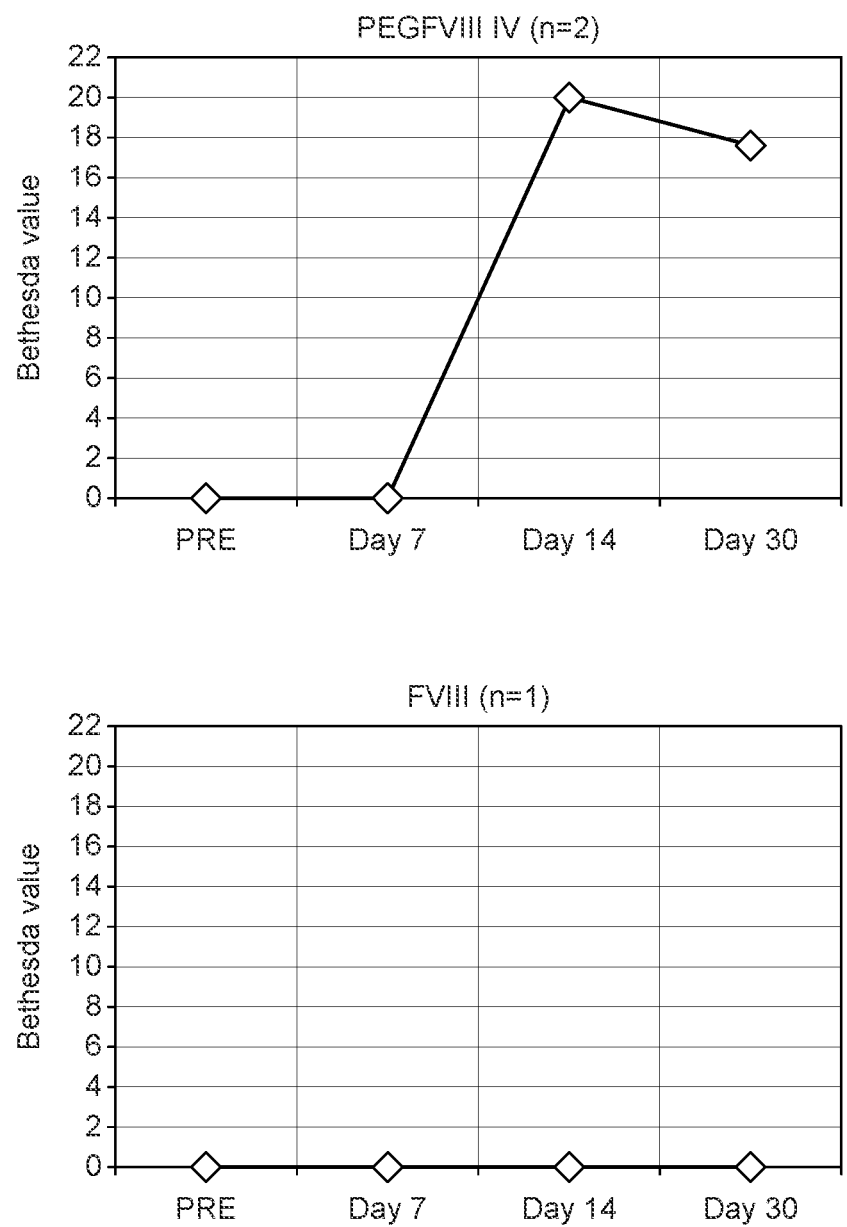
FIGS. 13A and 13B shows immune data (Bethesda value) for PEGFVIII administered subcutaneously (SQ) compared to intravenous (IV), number of subjects is given by "n".
Figure 13:
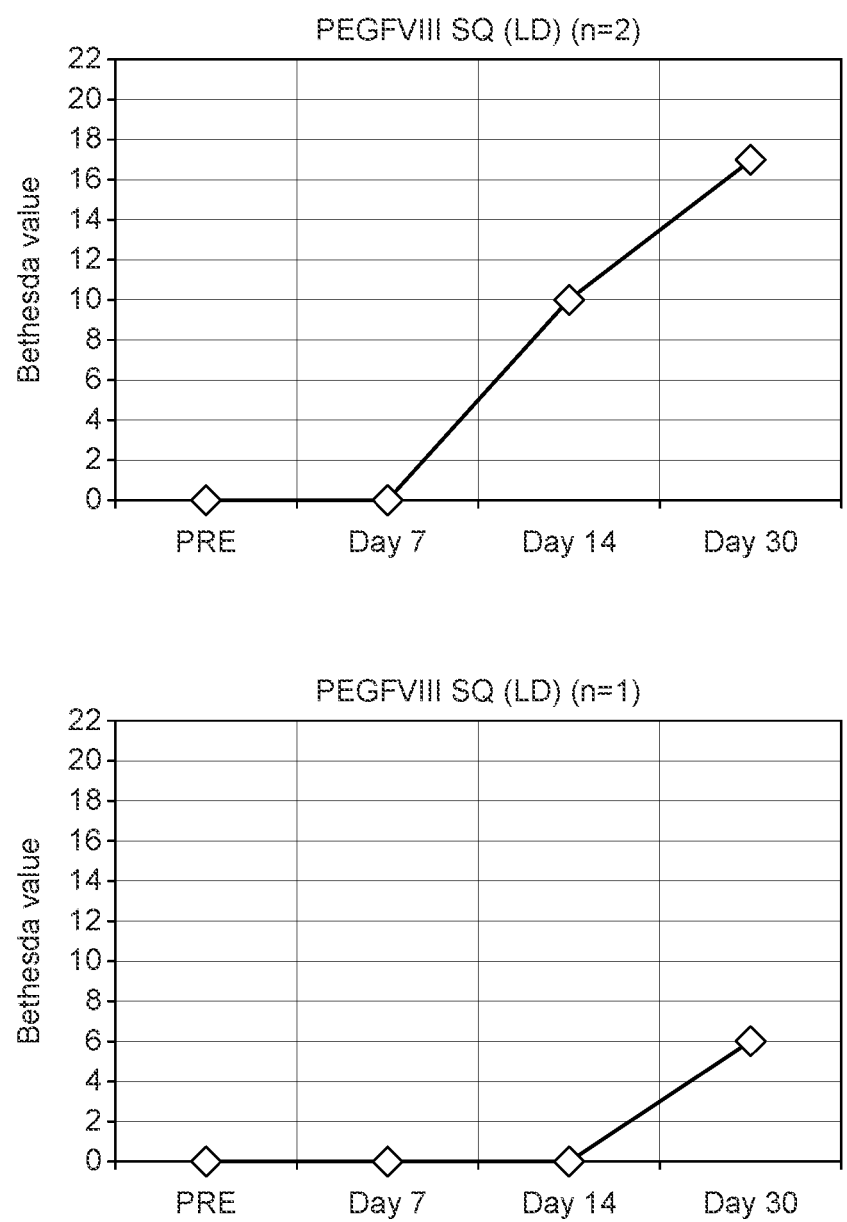

The plots in FIG. 13 demonstrate how much inhibitor activity has been found in blood plasma over time, as stimulated by the treatments. In the case of the direct IV treatment, there is a more rapid occurrence of a higher level of inhibitors, compared to SQ treatment which leaches into the system more slowly and is less provocative to the immune system.

Example 9: Comparative Studies on Subcutaneous Administration in Rats

This example describes the surprising depot effect encountered with blood factors when conjugated to polymers such as PEG. Moreover, the results show that it is possible to engineer the rate at which blood factors are made available from the subcutaneous space by manipulating the level of hydration imposed on the protein from the size (or amount) of PEG.

The relative pharmacokinetics of Factor VIIa PEGylated via 3 different forms of PEGylation was studied in rat subjects to compare their performance in terms of delivery from the subcutaneous space.

Native, recombinant Factor VIIa was administered to rat subjects, as well as 3 different PEGylated forms of FVIIa, either subcutaneously (SQ) or by intravenous (IV) administration:

a) TheraPEGylated FVIIa: FVIIa was mono-PEGylated to a 20 kDa PEG molecule using the "TheraPEG" technology of Polytherics Ltd (as described elsewhere and in WO 2011/135308);

b) GlycoPEGylated FVIIa: FVIIa was conjugated to PEG via standard glycoPEGylation technology giving a test product that was dominated by di-conjugated 20 kDa PEG with also some significant amounts of higher PEG products:

c) HATU-catalysed PEGylated FVIIa: FVIIa was monoPEGylated to a 20 kDa PEG (using a conjugation method derived from one described in U.S. Pat. No. 5,644,029).

TheraPEG-FVIIa 20 kDa PEG was dispersed to 10 mg/mL in 5 mM Na phosphate pH8.0, 15 mM NaCl, 2 mM EDTA. It was then incubated at 20° C. for 3 hours. A vial (5.3 mg) of FVIIa was reconstituted to 0.8 mg/mL in 20 mM sodium citrate pH6.0, 0.1M NaCl, 10 mM EDTA. It was incubated at 20° C. for 10 minutes. TCEP, 1.5 Molar Equivalents (ME) of 24 mM and 0.025ME of 0.4 mM SeCM were then added and incubated at 20° C. for 1 hour. 2 ME of activated PEG was then added to the reduced FVIIa. The mixture was incubated at 20° C. for 1 hour, and then at 5° C. for 17 hours. Size Exclusion Chromatography using a Superdex 200 column was then carried out in formulation buffer in order to purify the PEGylated FVIIa.

For analysis of the product, reconstituted rFVIIa, activated PEG, reaction mixture, and selected Superdex fractions (25, 30, 35, 39, 45, 51, 80) were run on non-reduced SDS-PAGE gels. Fractions containing PEGylated FVIIa were pooled and concentrated to approximately 3 mL prior to lyophilisation. The concentrated SEC pool was tested by reduced and non-reduced SDS PAGE, clotting activity and reversed phase HPLC assays both pre- and post-lyophilisation.

GlycoPEGylated FVIIa

A vial (5.3 mg) of rFVIIa was reconstituted in 2.5 mL MOPS buffered saline. The reconstituted rFVIIa was then buffer exchange on a PD10 desalting column into MOPS buffered saline and diluted to 1 mg/mL. The buffer exchanged rFVIIa was placed on ice and 100 mM sodium periodate was added to a final concentration of 2.5 mM. The mixture was incubated in the dark for a maximum of 30 minutes. Glycerol (50%) was the added to a final concentration of 3%. The mixture was then buffer exchanged into 0.1M sodium acetate buffer using a Zeba spin column. A 50 mg/mL stock solution of Amino oxy PEG was made and 10ME of this PEG was added to the desalted FVIIa. The reaction mixture was incubated at Room Temperature for 1-2 hours before further incubation at 4° C. overnight. The GlycoPEGylated FVIIa was then purified by SEC chromatography as described above.

For analysis of the product, selected SEC fractions (23, 27, 32, 35, 40, and 80) were run on non-reduced SDS-PAGE. Fractions containing GlycoPEGylated FVIIa were pooled and concentrated to approximately 3 mL prior to lyophilisation. The concentrated SEC pool was tested by reduced and non-reduced SDS PAGE, clotting activity and reversed phase HPLC assays both pre- and post-lyophilisation.

HATU PEG-FVIIa

A vial (5.3 mg) of rFVIIa was reconstituted in 2.5 mL borate buffer, buffer exchange on a PD10 column into borate buffer and dilute to 0.5 mg/mL. A stock solution of Methoxy-PEG was made up in acetonitrile to 16 mg/mL. The buffer exchanged rFVIIa was activated with 1.0ME of HATU and 2.5ME of DIEA for 10 minutes at room temperature. Following activation 8 ME of Methoxy-PEG was added to the activated rFVIIa over 2-5 minutes. The reaction mixture was then incubated at room temperature for 80-100 minutes. The HATU PEGylated FVIIa was then purified by SEC chromatography as described above.

For analysis of the product, selected SEC fractions were run on non-reduced SDS-PAGE. Fractions containing HATU PEGylated FVIIa were pooled and concentrated to approximately 3 mL prior to lyophilisation. The concentrated SEC pool was tested by reduced and non-reduced SDS PAGE, clotting activity and reversed phase HPLC assays both pre- and post-lyophilisation.

Method

Formulations at a dose of 0.5 mg/kg were administered either IV or SQ to Healthy rat subjects. For IV administration the appropriate volume of test article was injected into the tail vain. For SQ administration the appropriate volume of test article was injected into the scruff of the neck. Following administration of the control test articles (native rFVIIa) blood samples were taken at the following time intervals:

TABLE 24

| Time (h)   | 0.033 | 0.25 | 0.5 | 1 | 1.5 | 2 | 3 | 4 | 6 | 8 | 12 | 18 | 24 | 36 | 48 |
|------------|-------|------|-----|---|-----|---|---|---|---|---|----|----|----|----|----|
| IV control | ✓     | ✓    | ✓   | ✓ | ✓   | ✓ | ✓ | ✓ | ✓ | ✓ | ✓  | ✓  | ✓  |    |    |
| SQ control |       | ✓    | ✓   | ✓ |     | ✓ | ✓ | ✓ | ✓ | ✓ | ✓  | ✓  | ✓  | ✓  | ✓  |

Following administration of the test articles blood samples were taken at the following time intervals:

TABLE 25

| Time (h)   | 0.033 | 0.25 | 0.5 | 1 | 2 | 4 | 6 | 8 | 12 | 18 | 24 | 48 | 72 | 96 | 120 |
|------------|-------|------|-----|---|---|---|---|---|----|----|----|----|----|----|-----|
| IV article | ✓     | ✓    | ✓   | ✓ | ✓ | ✓ | ✓ | ✓ | ✓  | ✓  | ✓  | ✓  | ✓  | ✓  | ✓   |
| SQ article |       | ✓    | ✓   | ✓ | ✓ | ✓ | ✓ | ✓ | ✓  | ✓  | ✓  | ✓  | ✓  | ✓  | ✓   |

At each time point plasma was prepared from the blood sample and the FVIIa concentration determined using the Stago Asserachrom VII:Ag ELISA assay. This assay is an enzyme linked immunoassay procedure for the quantitative determination of Factor VII/VIIa concentration in plasma samples. The assay is a sandwich ELISA which comprises of microtitre wells pre-coated with a rabbit anti-human FVII antibody. Because the antibody has a different affinity for FVIIa than for PEG-FVIIa, a standard curve was prepared by dilution of a protein appropriate to the FVIIa that is present in the test plasma, i.e. rFVIIa (0.78 to 50 ng/ml) for assay of plasma from rats that were administered rFVIIa, or PEG-rFVIIa (0.78 to 50 ng/ml) for assay of plasma from dogs that were administered PEG-rFVIIa.

Plasma samples were diluted to an appropriate concentration to fall within the standard curve. Diluted plasma samples and standards were loaded and incubated at room temperature before washing and subsequent development with a rabbit anti-human FVII HRP conjugate and OPD (a colorimetric HRP substrate). The plate was read at 492 nm and the concentration of the test samples (ng/ml) is read from the standard curve. Results of the study are as shown in Table 26(a) and (b) where there are two routes of administration: intravenous (IV) and sub-cutaneous (SQ) for each of the PEGylated FVIIa molecules and a control arm which was the native FVIIa.

As shown in Table 26(a) and (b), there are 2 routes of administration, intravenous (IV) and subcutaneous (SQ) for each of the PEGylated FVIIa molecules and a control arm which was the native FVIIa.

This example describes the surprising depot effect encountered with blood factors when conjugated to polymers such as PEG. Moreover, the results show that it is possible to engineer the rate at which blood factors are made available from the subcutaneous space by manipulating the level of hydration imposed on the protein from the size (or amount) of PEG.

From the results shown in Table 26(a) and (b), it can be seen that:

All the PEGylated proteins have extended plasma half-lives by comparison to the naked protein The mono-PEG products, namely TheraPEG and HATU PEGylated proteins have a slower rate of entry to the plasma than the di-PEG conjugate (GlycoPEG) and therefore a more pronounced depot effect. This can be deduced by comparing the differences in the IV and SQ half-lives in each product.

For TheraPEG-FVIIa the IV t1/2 was 8.68 hours which compares to 23.2 hours for the same product given by SQ. This represents a 2.7-fold increase implying a very large depot effect for this mono-PEGylated product.

Similarly, for the mono-PEGylated HATU PEG-FVIIa the SQ t1/2 has an enhanced depot effect represented by a 1.7-fold increase over the IV t1/2 (24.3/14.07)

In contrast, for the heavily PEGylated product, Glyco-PEG-FVIIa, the half-lives for both products are closer to parity (22.3/19.34=1.15-fold) implying that the SQ administration of this product has little depot effect compared to IV administration.

In other words, the mono-PEGylated products when administered SQ would appear to have resisted being dispersed through the sub-cutaneous space for longer than the di-PEGylated product, thus providing the enhanced depot effect. The reduced amount of PEG on the mono-PEGylated products would leave more of the protein exposed; the greater PEG coverage on the GlycoPEG product would render it more water dispersible within the subcutaneous space, leading to a faster rate of entry via the lymphatic vessels into the plasma.

Surprisingly therefore, to achieve the longest duration of depot release, a lesser degree of PEGylation is required. Without being bound by theory, this can be rationalised by the lesser PEGylation exposing some of the protein to the subcutaneous tissue which confers a slow rate on the diffusion through the lymph. By contrast the higher degree of PEGylation covers the protein completely leaving the product free to quickly enter the blood circulation.

This supports the teaching that the modification of target molecules, in this case via PEGylation, may be tuned to exquisitely modify the release characteristics and thereby the concentration of the product in the blood over time and its bioavailability.

Overall, there is a very surprising total effect whereby the combination of PEGylation followed by subcutaneous delivery, renders an observed 35-fold increase in apparent half-life (0.66 hours for naked FVIIa to 23.2 hours following subcutaneous (SQ) administration).

Finally, it can be seen overall that the bioavailability favours the higher PEGylated species, namely GlycoPEG, confirming that the higher PEG and hydration levels promote a higher degree of mobility and therefore bioavailability.

TABLE 26 (a)

| Test Article | Dose route | Rat | Tmax (h) | Cmax (ng/ml) | AUC0-t (ng·h/ml) | AUC0-∞ (ng·h/ml) | t½ (h) |
|---|---|---|---|---|---|---|---|
| FVIIa | IV | 1 | 0.03 | 2251.8 | 600 | 624 | 0.55 |
|  |  | 2 | 0.03 | 2538.3 | 711 | 728 | 0.75 |
|  |  | 3 | 0.03 | 1892.3 | 533 | 561 | 0.66 |
|  |  | Mean | 0.03 | 2227.47 | 615 | 638 | 0.65 |
| TheraPEG-FVIIa | IV | 4 | 0.03 | 10024.5 | 33598 | 34021 | 8.97 |
|  |  | 5 | 0.03 | 8181 | 22051 | 22435 | 9.42 |

TABLE 26 (a)-continued

| Test Article | Dose route | Rat | Tmax (h) | Cmax (ng/ml) | AUC0-t (ng · h/ml) | AUC0-∞ (ng · h/ml) | t½ (h) |
|---|---|---|---|---|---|---|---|
| | | 6 | 0.03 | 10799.7 | 23251 | 23449 | 7.66 |
| | | Mean | 0.03 | 9668.40 | 26300 | 26635 | 8.68 |
| GlycoPEG-FVIIa | IV | 7 | 0.03 | 6647.2 | 55987 | 57138 | 21.24 |
| | | 8 | 0.03 | 5674.9 | 46702 | 47609 | 21.21 |
| | | 9 | 0.03 | 6227.3 | 47188 | 47663 | 15.57 |
| | | Mean | 0.03 | 6183.13 | 49959 | 50803 | 19.34 |
| HATU catalysed PEG-FVIIa | IV | 10 | 0.03 | 8090.5 | 31172 | 31775 | 13.49 |
| | | 11 | 0.03 | 7586.5 | 30448 | 31003 | 13.07 |
| | | 12 | 0.03 | 7557.1 | 35317 | 35697 | 15.66 |
| | | Mean | 0.03 | 7744.70 | 32312 | 32825 | 14.07 |

TABLE 26 (b)

| Test Article | Dose route | Rat | Tmax (h) | Cmax (ng/ml) | AUC0-t (ng · h/ml) | AUC0-∞ (ng · h/ml) | t½ (h) | Bioavailability (% AUC0-t SQ vs IV) |
|---|---|---|---|---|---|---|---|---|
| TheraPEG-FVIIa | SQ | 16 | 18.0 | 215.5 | 8015 | 9557 | 23.96 | 30.5 |
| | | 17 | 12.0 | 117.6 | 3695 | 4839 | 21.15 | 14.0 |
| | | 18 | 18.0 | 129.3 | 4227 | 5805 | 24.52 | 16.1 |
| | | Mean | 16.0 | 154.13 | 5312 | 6734 | 23.21 | 20.2 |
| GlycoPEG-FVIIa | SQ | 19 | 18.0 | 297.8 | 16868 | 17665 | 22.27 | 33.8 |
| | | 20 | 24.0 | 234.3 | 12471 | 13456 | 23.55 | 25.0 |
| | | 21 | 18.0 | 407.6 | 22243 | 22871 | 21.16 | 44.5 |
| | | Mean | 20.0 | 313.23 | 17194 | 17997 | 22.33 | 34.4 |
| HATU catalysed PEG-FVIIa | SQ | 22 | 18.0 | 224.8 | 10234 | 10996 | 20.85 | 31.7 |
| | | 23 | 18.0 | 138.7 | 5544 | 6750 | 28.03 | 17.2 |
| | | 24 | 18.0 | 249.1 | 11277 | 12147 | 24.03 | 34.9 |
| | | Mean | 18.0 | 204.20 | 9018 | 9964 | 24.30 | 27.9 |

The invention claimed is:

1. A method of treatment of haemophilia A in a human subject in need thereof, comprising:
   (a) subcutaneously administering a composition comprising 1 IU/kg to 50 IU/kg of a PEGylated Factor VIII, wherein the PEG is directly or indirectly conjugated to the Factor VIII via a serine or threonine residue, or via an amide, N-terminal amino group, or a carboxyl group; and
   (b) repeating the subcutaneous administration of the composition once-daily, twice-daily, less frequently than once daily, less frequently than twice daily, or before the concentration of the Factor VIII in the blood reduces to sub-therapeutic levels, in order to maintain a consistent therapeutic effect in the human subject,
   wherein plasma titers of Factor VIII are maintained above the 5% normal level of Factor VIII in a human subject not suffering from haemophilia A following sub-cutaneous administration for at least 48.5 hours after the subcutaneous administration.

2. A method of providing a sustained therapeutic effect of a therapeutic agent to a human subject in need thereof, comprising:
   (a) subcutaneously administering a composition comprising the therapeutic agent in a PEGylated form, wherein the PEG is directly or indirectly conjugated to the therapeutic agent via a serine or threonine residue, or via an amide, N-terminal amino group, or a carboxyl group, wherein the therapeutic agent is Factor VIII and wherein the composition comprises 1 IU/kg to 50 IU/kg of the therapeutic agent; and
   (b) repeating the subcutaneous administration of the composition once-daily, twice-daily, less frequently than once daily, less frequently than twice daily, or before the concentration of the therapeutic agent in the blood reduces to sub-therapeutic levels, in order to sustain the therapeutic effect in the human subject,
   wherein plasma titers of Factor VIII are maintained above the 5% normal level of Factor VIII in a human subject not suffering from haemophilia A following sub-cutaneous administration for at least 48.5 hours after the subcutaneous administration.

3. A method of delivering a consistent infusion of a therapeutic agent into the circulatory system of a human subject in need thereof, comprising:
   (a) subcutaneously administering a composition comprising the therapeutic agent in a PEGylated form, wherein the PEG is directly or indirectly conjugated to the therapeutic agent via a serine or threonine residue, or via an amide, N-terminal amino group, or a carboxyl group, wherein the therapeutic agent is Factor VIII and wherein the composition comprises 1 IU/kg to 50 IU/kg of the therapeutic agent; and
   (b) repeating the subcutaneous administration of the composition once-daily, twice-daily, less frequently than once daily, or less frequently than twice daily, without waiting for the concentration of the therapeutic agent in the bloodstream to reduce to sub-therapeutic levels, in order to deliver a consistent infusion of the therapeutic agent into the circulatory system of the human subject,
   wherein plasma titers of Factor VIII are maintained above the 5% normal level of Factor VIII in a human subject not suffering from haemophilia A following sub-cutaneous administration for at least 48.5 hours after the subcutaneous administration.

4. A method of delivering a prolonged and constant level of a therapeutic agent to the blood of a human subject in need thereof without increasing the incidence of a thrombotic event, comprising subcutaneously administering once-daily, twice-daily, less frequently than once daily, or less frequently than twice daily to the human subject a composition comprising the therapeutic agent in a PEGylated form, wherein the therapeutic agent is Factor VIII, wherein the composition comprises 1 IU/kg to 50 IU/kg of the therapeutic agent and wherein the PEG is directly or indirectly conjugated to the therapeutic agent via a serine or threonine residue, or via an amide, N-terminal amino group, or a carboxyl group, wherein plasma titers of Factor VIII are maintained above the 5% normal level of Factor VIII in a human subject not suffering from haemophilia A following sub-cutaneous administration for at least 48.5 hours after the subcutaneous administration.

5. A method of treatment of haemophilia A in a human subject in need thereof, comprising subcutaneously administering once-daily, twice-daily, less frequently than once daily, or less frequently than twice daily to the human subject a composition comprising a PEGylated therapeutic agent, wherein the PEG is directly or indirectly conjugated to the therapeutic agent via a serine or threonine residue, or via an amide, N-terminal amino group, or a carboxyl group, and wherein the therapeutic agent is Factor VIII, wherein the composition comprises 1 IU/kg to 50 IU/kg of the therapeutic agent, in order to deliver a prolonged and constant level of the therapeutic agent to the blood of the human subject without increasing the ratio $C_{max}:C_{average}$, wherein plasma titers of Factor VIII are maintained above the 5% normal level of Factor VIII in a human subject not suffering from haemophilia A following sub-cutaneous administration for at least 48.5 hours after the subcutaneous administration.

* * * * *